United States Patent [19]

Yamashita et al.

[11] 3,954,840

[45] May 4, 1976

[54] 1,3,5,7-NAPHTHALENETETRACARBOXYLIC ACIDS AND PROCESS FOR PREPARATION THEREOF

[75] Inventors: Gentaro Yamashita, Iwakuni; Yasushi Tsuru, Matsuyama; Kiyoshi Yamamoto, Iwakuni; Moriharu Yamamoto, Matsuyama; Nobuo Sakaiya, Matsuyama; Toshihiro Aoyama, Matsuyama; Tadao Komoriya, Iwakuni, all of Japan

[73] Assignee: Teijin Ltd., Osaka, Japan

[22] Filed: Feb. 11, 1974

[21] Appl. No.: 441,626

[30] Foreign Application Priority Data

| Feb. 14, 1973 | Japan | 48-17420 |
| Feb. 15, 1973 | Japan | 48-17894 |
| Mar. 3, 1973 | Japan | 48-25399 |
| Mar. 3, 1973 | Japan | 48-25400 |
| Mar. 19, 1973 | Japan | 48-30872 |
| Mar. 19, 1973 | Japan | 48-30873 |
| Mar. 29, 1973 | Japan | 48-35035 |

[52] U.S. Cl. ............ 260/475 FR; 260/429.9; 260/475 B; 260/515 P; 260/525
[51] Int. Cl.² ............... C07C 63/40; C07C 69/76
[58] Field of Search ............ 260/475 FR, 515 P

[56] References Cited

UNITED STATES PATENTS

| 2,849,482 | 8/1958 | Raecke et al. | 260/515 |
| 3,042,717 | 7/1962 | Schenk | 260/515 |
| 3,101,368 | 8/1963 | Schenk | 260/515 |
| 3,255,235 | 6/1966 | Coran et al. | 260/475 |
| 3,320,303 | 5/1967 | Schenk et al. | 260/475 |
| 3,746,752 | 7/1973 | Kuper | 260/515 |

FOREIGN PATENTS OR APPLICATIONS

| 47-37947 | 9/1972 | Japan | 260/515 |
| 42-23183 | 10/1967 | Japan | 260/475 |

OTHER PUBLICATIONS

McNelis, J. Org. Chem., Vol. 30, pp. 1209–1213, (1965).

Primary Examiner—Anton H. Sutto
Assistant Examiner—Jane S. Myers
Attorney, Agent, or Firm—Sherman & Shalloway

[57] ABSTRACT

A novel 1,3,5,7-naphthalenetetracarboxylic acid, an alkali salt thereof, or an ester thereof, and a novel process for preparation thereof, and method of effective purification thereof.

14 Claims, 6 Drawing Figures

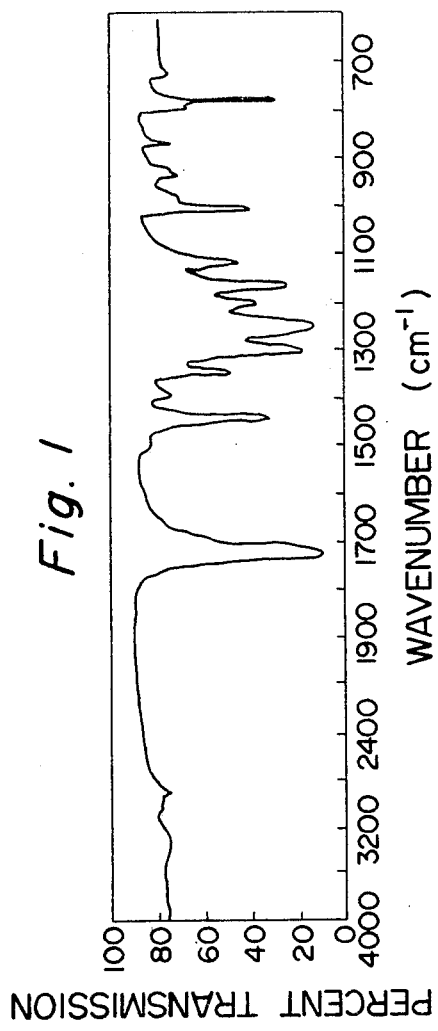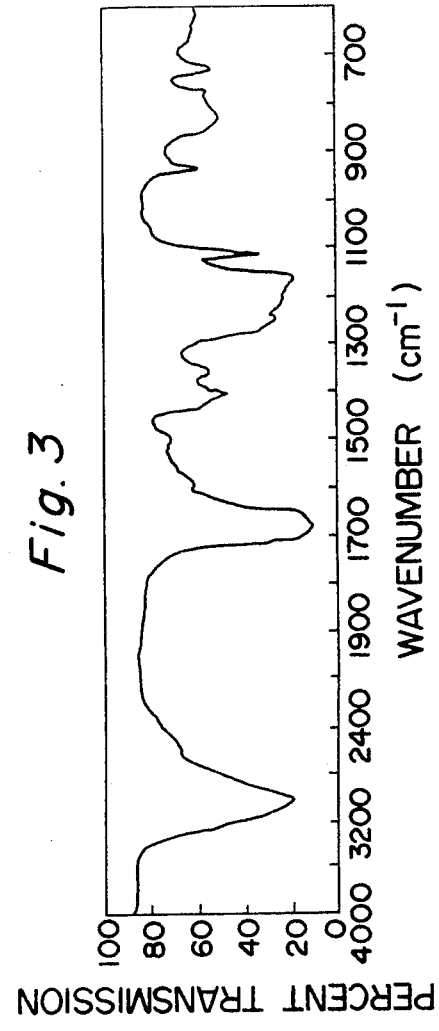

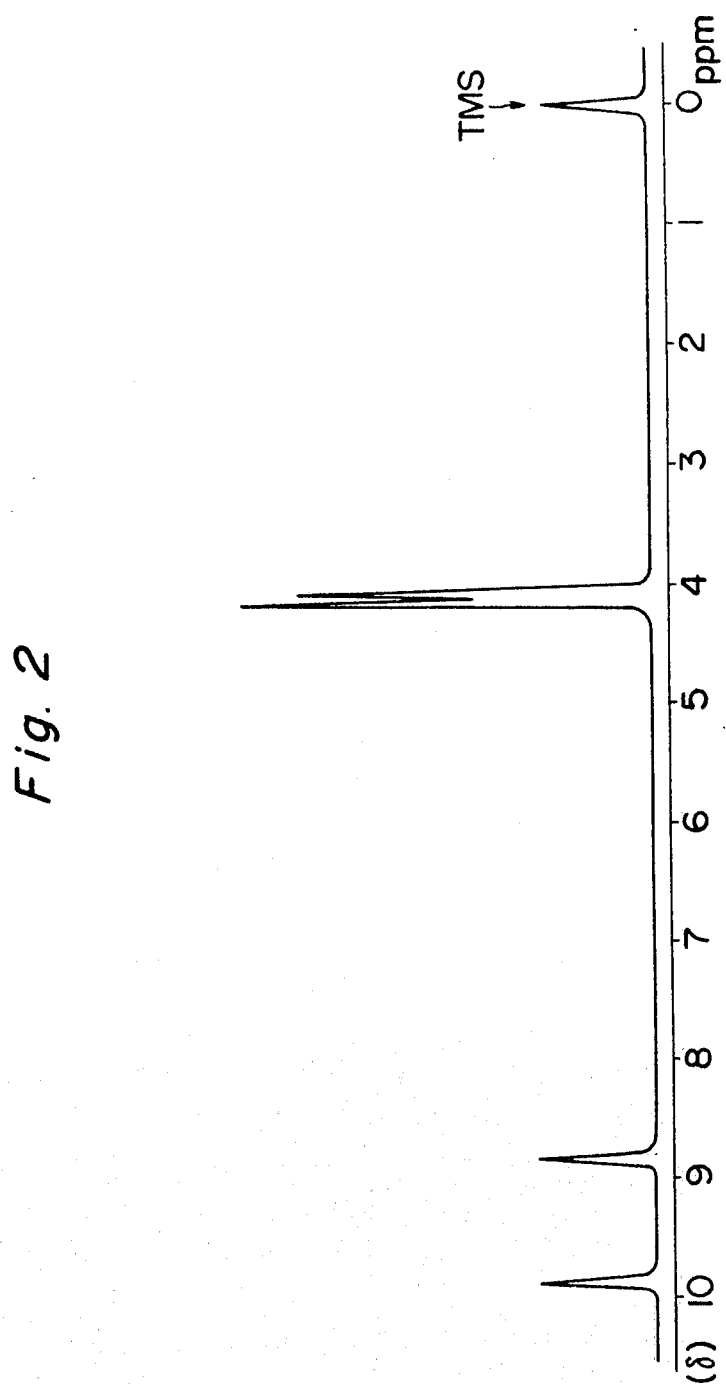

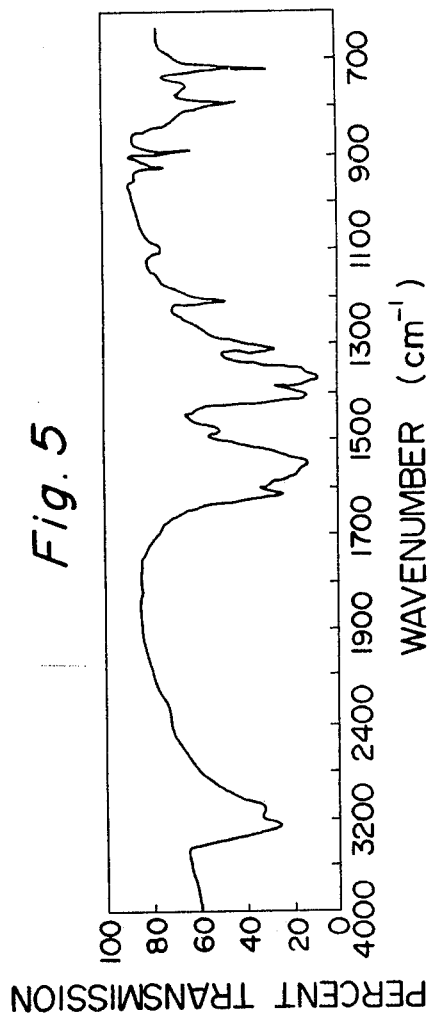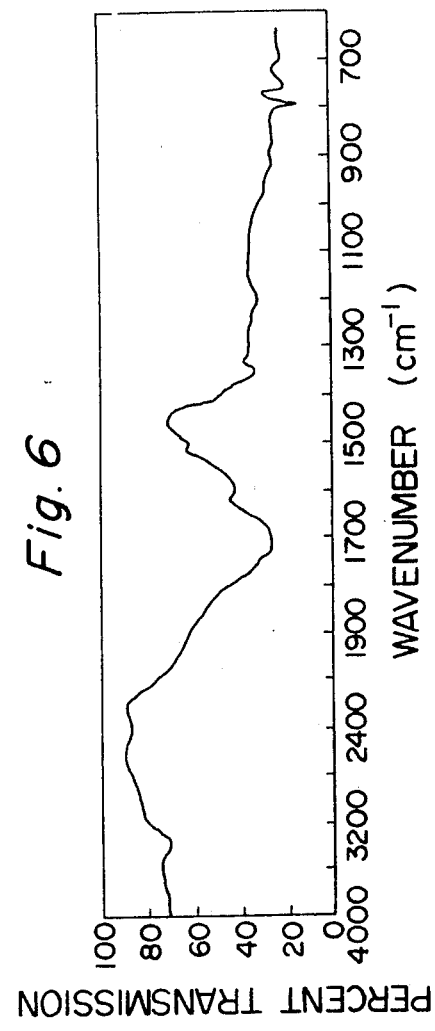

1,3,5,7-NAPHTHALENETETRACARBOXYLIC ACIDS AND PROCESS FOR PREPARATION THEREOF

This invention relates to 1,3,5,7-naphthalenetetracarboxylic acids, and more specifically to novel 1,3,5,7-naphthalenetetracarboxylic acid, its alkali salts and its esters. The invention also relates to processes for preparing and separating 1,3,5,7-naphthalenetetracarboxylic acid, its alkali salts and its esters.

Theoretically, there are 22 isomers of naphthalenetetracarboxylic acid, and a considerable number of them, for example, 1,4,5,8- and 2,3,6,7-naphthalenetetracarboxylic acids, have already been synthesized and known. However, 1,3,5,7-naphthalenetetracarboxylic acid of the formula

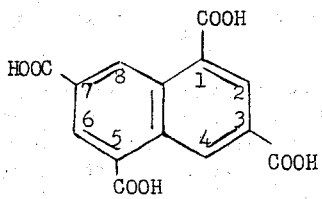

has not been known to exist, and is a novel compound which has been synthesized for the first time by the present inventors.

Accordingly, the present invention provides 1,3,5,7-naphthalenetetracarboxylic acid of the above formula (I), and its alkali salts and esters.

The 1,3,5,7-naphthalenetetracarboxylic acid is a kind of aromatic tetracarboxylic acid having very good symmetry, and has excellent thermal stability. It is useful as a material for producing thermally stable unsaturated polyesters, allyl resins, and plasticizers, etc.

The alkali salt of 1,3,5,7-naphthalenetetracarboxylic acid may be not only in the form of a tetraalkali salt, but also in the form of a mono-, di-, or tri-alkali salt. The alkali for forming these alkali salts may be any conventional alkalies which form salts together with organic carboxylic acids, for example alkali metals, ammonia or organic amines, the alkali metal being especially preferred.

The 1,3,5,7-naphthalenetetracarboxylic acid of this invention may also be in the form of esters. The suitable esters are those in which the ester residue is a monovalent hydrocarbon group, especially an alkyl group.

Thus, the 1,3,5,7-naphthalenetetracarboxylic acid of this invention, and suitable classes of its alkali salts and esters can be expressed by the following formula

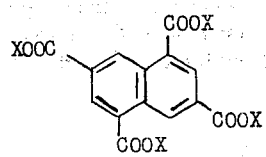

wherein the four X groups are simultaneously hydrogen atoms, alkali metals, alkyl groups or alkenyl groups; or 1 to 3 of X groups are alkali metals, alkyl groups or alkenyl groups and the remainder a hydrogen atom.

Examples of the alkali metals include sodium, potassium, lithium, and beryllium, the sodium and potassium being especially preferred. The alkyl groups and alkenyl groups may either be of straight-chain or branched-chain. Those having 1 to 12 carbon atoms, especially 1 to 4 carbon atoms, are suitable. Examples include methyl, ethyl, n-or iso-propyl, n-, sec.-, iso-, or tert.-butyl, n-, sec.-, or neo-pentyl, n-hexyl, n-octyl n-dodecyl and allyl.

Some typical examples of the compounds of this invention corresponding to the above formula (II) are given below. It should be noted however that these examples do not limit the present invention.

1. Free acid 1,3,5,7-naphthalenetetracarboxylic acid

2. Tetraalkali salts or tetraesters

Tetrapotassium 1,3,5,7-naphthalenetetracarboxylate,
Tetrasodium 1,3,5,7-naphthalenetetracarboxylate,
Tetramethyl 1,3,5,7-naphthalenetetracarboxylate,
Tetraethyl 1,3,5,7-naphthalenetetracarboxylate,
Tetraisopropyl 1,3,5,7-naphthalenetetracarboxylate,
Tetra-n-butyl 1,3,5,7-naphthalenetetracarboxylate,
Tetra-n-hexyl 1,3,5,7-naphthalenetetracarboxylate,
Tetra-n-octyl 1,3,5,7-naphthalenetetracarboxylate,
Tetra-n-dodecyl 1,3,5,7-naphthalenetetracarboxylate,
Tetraallyl 1,3,5,7-naphthalenetetracarboxylate.

3. Tri-alkali salts or -esters 1,3,7-Tripotassium 1,3,5,7-naphthalenetetracarboxylate,
1,3,7-Trisodium 1,3,5,7-naphthalenetetracarboxylate,
1,3,5-Trimethyl 1,3,5,7-naphthalenetetracarboxylate,
1,3,7-Tri-n-butyl 1,3,5,7-naphthalenetetracarboxylate, 4. Di-alkali salts or -esters The di-alkali salts or -esters include 1,3-, 1,5-, and 3,7-di-salts or -esters. Of the dialkali salts of this invention, symmetrical 3,7-dialkali salts of the formula

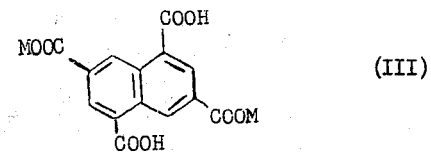

wherein M is an alkali metal, especially potassium or sodium, are of especial interest in the present invention. These symmetrical dialkali salts of the formula (III) can be easily prepared from the tetraalkali salts of this invention by the method to be described, and have a wide range of utility, for example, as intermediates for synthesizing dyes, pigments, and fluorescent brightening agents, materials for preparing various polymers, plasticizers, lubricant oils, or as additives.

Examples of suitable dialkali salts of the formula (III) are 3,7-dipotassium 1,3,5,7-naphthalenetetracarboxylate and 3,7-disodium 1,3,5,7-naphthalenetetracarboxylate.

5. Mono-alkali salts or -esters

1-Potassium 1,3,5,7-naphthalenetetracarboxylate,
3-Sodium 1,3,5,7-naphthalenetetracarboxylate,
1-Methyl 1,3,5,7-naphthalenetetracarboxylate,
3-Ethyl 1,3,5,7-naphthalenetetracarboxylate.

As stated above, 22 isomers of naphthalenetetracarboxylic acid could exist theoretically. Of these, a known tetracarboxylic acid, for example, 1,4,5,8- or 2,3,6,7-naphthalenecarboxylic acid, it is reported, can be synthesized in the following way.

i. Preparation of 1,4,5,8-naphthalenetetracarboxylic acid:
  a. Method comprising oxidizing pyrene with an alkali bichromate in the presence of sulfuric acid [German Patent 601,104 (1943)].
  b. Method comprising oxidizing pyrenequinone with hypochlorous acid [French Pat. No. 783,121 (1935), and German Pat. No. 658,352 (1938)].

ii. 2,3,6,7-naphthalenetetracarboxylic acid or its dianhydride can be obtained by the method disclosed in U.S. Pat. No. 2,912,442 (1959) which comprises dehydrogenerating 1,2,3,4,5,6,7,8-octahydro-2,3,6,7-naphthalenetetracarboxylic dianhydride using bromine in trichlorobenzene, and hydrolyzing the resulting 2,3,6,7-naphthalenetetracarboxylic dianhydride.

However, the 1,3,5,7-naphthalenetetracarboxylic acid of this invention is difficult to synthesize by such conventional techniques, and no successful synthesis of this compound has ever been reported.

Surprisingly, we have found that when alkali salts of naphthalenecarboxylic acids other than 1,3,5,7-naphthalene tetracarboxylic acid are subjected to a heat rearrangement reaction which is known per se as the Henkel method (see German Pat. Nos. 932,125, 949,652, and 1,002,316), alkali salts of 1,3,5,7-naphthalenetetracarboxylic acids can be prepared very easily in good yields.

Thus, according to this invention, there is provided a process for preparing alkali metal salts of 1,3,5,7-naphthalenetetracarboxylic acid expressed by the formula

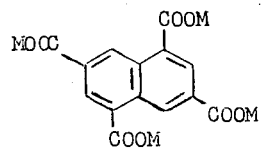

(IV)

wherein M is an alkali metal, which comprises heating an alkali metal salt of at least one naphthalenecarboxylic acid of the formula

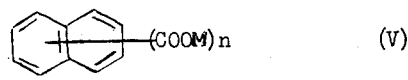

(V)

wherein $n$ is an integer of 1 to 4; and M is an alkali metal with the provisio that when $n$ is 4, the four —COOM groups are not present simultaneously at the 1,3,5,7-positions to a temperature of at least 350°C. in an atmosphere of an inert gas.

The alkali metal salt of the naphthalenecarboxylic acid of the formula (V) is especially preferably potassium salts, and may include, for example, potassium 1- or 2-naphthoate, dipotassium 1,2-, 1,3-, 1,4-, 1,5-, 1,6-, 1,7-, 1,8-, 2,3-, 2,6-, or 2,7-naphthalenedicarboxylate, tripotassium 2,3,6- or 1,3,7-naphthalenetricarboxylate, and tetrapotassium 1,2,3,4-, 1,2,4,5-, 1,2,5,8-, 2,3,6,7- or 1,4,5,8-naphthalenetetracarboxylate.

These alkali metal salts of naphthalenecarboxylic acid may be used either alone or as a mixture of two or more.

When the alkali metal salt of naphthalenecarboxylic acid of formula (V) is heated, rearrangement or disproportionation or both occur according to the type of the alkali metal carboxylate used as the starting material to form the desired tetraalkali metal 1,3,5,7-naphthalenetetracarboxylates of formula (IV).

The reaction is usually carried out in an atmosphere of an inert gas. Carbon dioxide gas is most commonly used as the inert gas, but other inert gases such as nitrogen, helium or argon may also be used.

The heating temperature can be varied over a wide range depending upon the type of the starting material, and other reaction conditions, but is usually at least 350°C. Preferred temperatures are 400° to 500°C.

Generally, it is preferred to carry out the above rearrangement and/or disproportionation reaction in the presence of a catalyst. The catalyst that can be used may be any conventional catalysts used for the Henkel rearrangement. Suitable catalysts are, for example, halides, oxides, sulfates, carbonates, or carboxylates of metals such as cadmium, zinc or iron. The amount of the catalyst to be used is about 1 to 10 mol% based on the alkali metal carboxylate of the starting formula (V). A promotor such as a carbonate or halide of the alkali metal may also be added together with the above catalyst.

The reaction can usually be performed at atmospheric pressure or at an elevated pressure without using a solvent. The preferred elevated pressure is about 5 to 100 Kg/cm². Furthermore, the reaction can be performed batchwise in a closed system, for example, in an autoclave, or continuously while blowing an inert gas into the reaction system.

Thus, tetraalkali metal salts of 1,3,5,7-naphthalenetetracarboxylic acid having good symmetry can be obtained from the alkali metal naphthalenecarboxylates of the formula (IV). These alkali metal salts can be separated from the reaction mixture by the method to be described. Or they can be converted to the corresponding free tetracarboxylic acid or tetraesters by acid precipitation or esterification.

We have also found that when a mixture consisting of the alkali metal naphthalenecarboxylate of the formula (V) and at least 0.1% by weight, preferably 1 to 40% by weight, more preferably 2 to 20% by weight, of alkali metal salt, zinc salt or cadmium salt of 1,3,5,7-naphthalenetetracarboxylic acid is used as the starting material, the rearrangement and/or disproportionation reaction can be markedly promoted to give the desired tetra alkali metal 1,3,5,7-naphthalenetetracarboxylate of the formula (IV) in a much better yield.

The alkali salt, zinc salt or cadmium salt of 1,3,5,7-tetracarboxylic acid to be included in the above mixture need not to be pure, but may be in the crude form. Or the reaction mixture obtained by the process of the invention described above can be used as such. Thus, by adding at least one alkali metal naphthalenecarboxylate of the formula (V) further to the reaction mixture obtained by the process of the invention described above, and continuing the reaction, the desired product can be obtained in a high yield. Alternatively, the process of this invention can be performed using a mixture prepared by adding a separately prepared alkali salt, zinc salt or cadmium salt of 1,3,5,7-naphthalenetetracarboxylic acid to a starting material composed of at least one alkali metal naphthalenecarboxylate of the formula (V).

The heat rearrangement and/or disproportionation reaction using the above starting mixture can be carried out under the same conditions as described above.

According to the process of this invention described above, tetra alkali metal 1,3,5,7-naphthalenetetracarboxylates can be obtained easily in good yields. The alkali metal 1,3,5,7-naphthalenetetracarboxylates so prepared can be separated from the reaction mixture and purified by various procedures. For example, the tetraalkali metal 1,3,5,7-naphthalenetetracarboxylate(to be often abbreviated as "$M_4XA$") produced by the process of this invention can be advantageously separated from the reaction mixture and purified by the following procedures.

1. Water extraction

The reaction mixture obtained by the process of this invention generally contains the unreacted alkali metal naphthalenecarboxylate used as a starting material, the reaction intermediates, other alkali metal naphthalenecarboxylates, naphthalene and carbonaceous materials formed as by-product, and the catalyst, etc., in addition to the resulting $M_4XA$. It is therefore not easy to separate $M_4XA$ effectively from such a reaction mixture. It has been found however that mere contacting of this reaction mixture with a suitable amount of water results in the selective extraction of $M_4XA$ into water.

Generally, alkali metal naphthalenecarboxylates, taken individually, are easily soluble in a sufficient amount of water. It is surprising to note that when the above reaction mixture containing $M_4XA$ is brought into contact with an insufficient amount of water which does not completely dissolve the alkali metal naphthalenecarboxylates contained in it, $M_4XA$ alone is selectively extracted; that the solubilities of alkali metal salts of naphthalenedicarboxylic acids or naphthoic acid in the aqueous solution containing $M_4XA$ extracted therein are remarkably reduced; and accordingly that the resulting aqueous solution contains a large quantity of $M_4XA$ with low contents of the starting materials such as the alkali naphthoate or naphthalene dicarboxylates, the intermediates, or the by-product alkali naphthalenecarboxylates. This will be clear from the solubilities of potassium naphthalenecarboxylate measured at 30°C., as shown in Table 1 below.

Table 1

| | |
|---|---|
| Solubility of potassium 2-naphthoate in 100 g of pure water | 80 g |
| Solubility of potassium 2-naphthoate in 100 g of a 30% by weight aqueous solution of tetrapotassium 1,3,5,7-naphthalene-tetracarboxylate | 0.3 g |
| Solubility of dipotassium 2,6-naphthalene-dicarboxylate in 100 g of pure water | 32 g |
| Solubility of dipotassium 2,6-naphthalene-dicarboxylate in 100 g of a 30% by weight aqueous solution of tetrapotassium 1,3,5,7-naphthalenetetracarboxylate | 1.0 g |

When the amount of water is too large in extracting the reaction mixture containing $M_4XA$ with water, the amounts of other alkali metal naphthalenecarboxylates extracted increase. Accordingly, it is desirable to use suitable amounts of water. The amount of water to be use also depends upon the composition of the reaction mixture or the content of $M_4XA$ in the reaction mixture. If a water-soluble alkali metal compound such as the carbonate, hydrogencarbonate, sulfate, halide, or hydroxide is present, an aqueous solution of such a compound has an action of remarkably decreasing the solubility of the alkali metal salts of naphthalenecarboxylic acids other than $M_4XA$. Accordingly, when the reaction mixture contains these compounds, or an aqueous solution containing the above alkali metal compound is used as an extraction medium, it is possible to extract $M_4XA$ selectively without hardly any content of alkali metal naphthoates or dialkali metal naphthalenedicarboxylates even if a large quantity of the extracting medium is used.

For example in the case of potassium salt, if it is desired to obtain high purity $M_4XA$ by extracting with water the thermal rearrangement and/or disproportionation reaction product containing the potassium salt as product and the unreacted starting material and small amounts of by-product potassium compounds such as potassium carbonates or halides, the suitable amount of water is 2 to 10 times, preferably 2.5 to 5 times, the weight of the tetrapotassium 1,3,5,7-naphthalenetetracarboxylate. On the other hand, if the thermal rearrangement and/or disproportionation reaction mixture contains considerable amounts of inorganic potassium salts such as potassium carbonate or potassium chloride or an aqueous solution containing inorganic potassium salts is used as an extracting medium, the suitable amount of water is 2 to 10 times, preferably 2.5 to 5 times, the total weight of the inorganic potassium salts and tetrapotassium 1,3,5,7-naphthalenetetracarboxylate, although somewhat varying according to the type of the inorganic potassium salt.

Generally, the higher the extracting temperature, the greater the solubility of $M_4XA$, and the more rapid is the extraction of $M_4XA$ from the thermal rearrangement and/or disproportionation reaction mixtures. However, the solubilities of alkali salts of naphthalenecarboxylic acids other than $M_4XA$ increase with higher extracting temperatures. In such a case, therefore, it is desirable to separate $M_4XA$ after precipitating the other alkali metal naphthalenecarboxylates by cooling or concentrating the extract. Especially when alkali carbonates and halogenated alkali salts are present in great amounts, the solubilities of naphthalenecarboxylic acids other than $M_4XA$ become very small. Therefore, even if the separation is carried out at a temperature near the boiling point at atmospheric pressure, $M_4XA$ is extracted selectively, and cooling the extract as obtained affords substantially pure $M_4XA$ precipitate.

The extract of $M_4XA$ obtained by solid-liquid separation of the extract residue after extracting the thermal rearrangement and/or disproportionation reaction products with water or an aqueous solution containing an alkali metal compound can be used directly as aqueous solution for the intended use. For example, it may be precipitated with a mineral acid to form free 1,3,5,7-naphthalenetetracarboxylic acid.

Furthermore, the extract is concentrated and/or cooled to precipitate $M_4XA$, and solid $M_4XA$ can be used for various end uses.

The separating effect can be increased by applying conventional purifying techniques, for example, by bringing the extract of $M_4XA$ into contact with activated carbon.

2. Concentrating Separation

The solubilities of some of the alkali metal naphthalenecarboxylates in water are greatly affected by the concentration of the alkali ions in the aqueous solution. The solubility of, for example, the alkali metal 1,3,5,7-naphthalenetetracarboxylate ($M_4XA$) of this invention does not so much change according to the alkali ion concentrations, but the dialkali metal 2,6-naphthalenedicarboxylates markedly decrease in solubility with increasing alkali ion concentrations. The concentrating separation method described here is a method of separating $M_4XA$ of high purity by utilizing the difference in solubility at a specific alkali ion concentration between $M_4XA$ and the other alkali metal naphthalenecarboxylates. This method comprises dissolving the thermal rearrangement and/or disproportionation reaction mixtures obtained as described above in water, evaporating off water from the resulting aqueous solution and/or adding alkali to the aqueous solution, to adjust the alkali ion concentration of the aqueous solution to at least 6 g per 1000 g of water, hot filtering the precipitated solid substance, and precipitating $M_4XA$ from the resultant filtrate.

According to this method, the reaction mixture from the thermal rearrangement and/or disproportionation reactions is first dissolved in cold or warm water to form a 10–20% by weight aqueous solution, and if desired, solid insoluble substances such as by-product carbonaceous materials or the catalyst are removed from the aqueous solution by filtration. The aqueous solution is, if desired, treated with activated carbon to remove coloring substances, and then the alkali ion concentration of the aqueous solution is adjusted to at least 6 g-alkali ion/1000 g-water.

The adjustment of the alkali ion concentration of the aqueous solution can be performed by evaporating off water from the aqueous solution, or adding an alkali metal compound such as an alkali carbonate, alkali hydrogencarbonate, an alkali hydroxide or an alkali halide, or a mixture of these to the aqueous solution, or by using both of these procedures.

In order to obtain $M_4XA$ of high purity, it is important that the above aqueous solution is treated until its alkali ion concentration is adjusted to at least 6 g-alkali ion/1,000 g-water.

There is no particular restriction on the upper limit of the alkali ion concentration, but if the concentration is too high, $M_4XA$ becomes precipitated, and the yield of $M_4XA$ to be obtained in the subsequent cooling step decreases.

Generally, the concentration should not exceed 12 g-alkali ion/1,000 g-water, and most preferably the concentration is 6 to 10 g-alkali ion/1,000 g-water.

By the adjustment of the alkali ion concentration, substances such as other alkali metal naphthalenecarboxylates which have lower solubility in the aqueous solution than $M_4XA$ are precipitated as solids. If the alkali ion concentration does not reach above-specified level, substances other than $M_4XA$ remain in the mother liquor in great amounts and become a cause of reducing the purity of $M_4XA$ to be separated in the subsequent cooling step. If, conversely, the amounts of the solids to be precipitated in this adjusting step are increased the purity of $M_4XA$ to be obtained in the subsequent cooling step increases accordingly. But if the amounts of the solids are too large, the yield of $M_4XA$ decreases. The optimum amount of the solids to be precipitated in this step would be easily determined by any one skilled in the art on the basis of routine tests.

The solids precipitated are hot filtered, and $M_4XA$ is precipitated from the resulting filtrate and recovered. The temperature during the hot filtration differs according to the type of the reaction mixture, or the alkali ion concentration, but is generally at least 80°C., preferably 90°C and up to the boiling point at atmospheric pressure.

The precipitation of $M_4XA$ from the resulting filtrate can be performed by cooling the filtrate as obtained, or concentrating the filtrate, or adding the alkali metal compound mentioned above to the filtrate, or by combining these procedures.

The extent of concentrating is not critical, but usually the concentration is performed to an extent that the alkali ion concentration in the aqueous solution is not more than 15 g ion/100 g - $H_2O$.

The amount of the alkali to be added to the filtrate is also not critical, but usually it is preferred to select it so that the alkali concentration of the mother liquor after cooling becomes about 3 – 6 g - ion/100 g - mother liquor.

Experiments were carried out which comprises the steps of dissolving the rearrangement and/or disproportionation reaction mixture in water, removing solid insoluble substances such as carbonaceous materials or catalyst from the aqueous solution, treating the filtrate obtained with activated carbon, adding potassium carbonate ($K_2CO_3$) to the aqueous solution to adjust its potassium ion concentration to the value shown in Table 2, hot filtering the aqueous solution at a temperature of 95°C., adding potassium carbonate further to the resulting filtrate, cooling the mixture to room temperature, and filtering it. The following table 2 shows the relation between the purity and the yield of the potassium 1,3,5,7-naphthalenetetracarboxylate ($K_4XA$) present in the resulting cake.

Table 2

| Experiments | Runs | Extent of concentration* (g-K ion/1000 g-water) | Concentration of $K_2CO_3$** (g-K ion/1000 g-water) | Purity (wt.%) | Yield (wt.%) |
| --- | --- | --- | --- | --- | --- |
| I | 1 | 4.8 | 2.6 | 78.6 | 98.3 |
|   | 2 | 7.4 | 2.6 | 98.8 | 98.0 |
|   | 3 | 8.5 | 2.6 | 99.7 | 90.1 |
| II | 1 | 7.1 | 5.2 | 82.4 | 99.0 |
|    | 2 | 8.6 | 5.2 | 98.3 | 97.9 |
|    | 3 | 10.9 | 5.2 | 99.9 | 83.4 |
| III | 1 | 8.6 | 6.4 | 90.3 | 98.9 |
|     | 2 | 9.2 | 6.4 | 98.9 | 98.4 |
|     | 3 | 10.9 | 6.4 | 99.7 | 87.7 |

Note
* The "extent of concentration" means the potassium ion concentration in the concentrated mother liquor to be submitted to hot filtration.
**The "concentration of $K_2CO_3$" is the potassium ion concentration based on the potassium carbonate in the concentrated mother liquor.

It is seen from the results shown in Table 2 above that the purity and yield of $K_4XA$ are affected by the $K_2CO_3$ concentration of the extent of concentration and the $K_2CO_3$ concentration of the concentrated mother liquor, and thus, it is expected that the extent of concentration and the $K_2CO_3$ concentration in Run 2 of each of the Experiments I, II and III are most suitable for obtaining $K_4XA$ in high purity and yield.

From the extent of concentration and the $K_2CO_3$ concentration in Run 2 of each of the Experiments I, II and III, it will be seen that the extent of concentration and the $K_2CO_3$ concentration preferably have the following relationship.

$$y = 0.5x + 6 \qquad (1)$$

wherein $y$ is the total K ion concentration (g-ion/1000 g of water) of the concentrated mother liquor, and $x$ is the ion concentration (g-ion/1000 g of water) ascribable to $K_2CO_3$ in the concentrated mother liquor.

The following Table 3 shows the solubility of $K_4XA$ in an aqueous solution of potassium carbonate (the grams of the potassium salt dissolved in 100 g of solvent).

Table 3

| $K_2CO_3$ concentration (g-potassium ion/100 g of solvent) | Solubilities at 60°C. | Solubilities at 30°C. |
| --- | --- | --- |
| 0 | 57.0 | 48.8 |
| 1.45 | 41.7 | 33.7 |
| 2.90 | 25.5 | 18.1 |
| 4.35 | 9.7 | 2.8 |

It is seen from Table 3 that lower temperatures are more preferred, and if the aqueous solution having a potassium carbonate concentration of 4.35 g/1000 g of aqueous solution is cooled to 30°C., virtually all of the $K_4XA$ is precipitated. Cooling can be effected in this invention by any known procedure.

The alkali metal 1,3,5,7-naphthalenetetracarboxylate precipitated by cooling is separated by filtration, for example.

3. Addition of Alcohol

The $M_4XA$ separated by the water extraction method described in paragraph (1) or (2) frequently contains significant amounts of alkali naphthalenecarboxylates such as dialkali 2,6-naphthalenedicarboxylates or alkali 2-naphthoates, and may often be unsatisfactory where the intended use requires pure 1,3,5,7-naphthalenetetracarboxylic acid.

We have found that by treating the crude $M_4XA$ with an aliphatic alcohol such as methanol, ethanol, propanol or butanol or a mixture of these with water as a purifying medium, high purity $M_4XA$ not containing alkali salts of naphthalenedi- or mono-carboxylic acids can be easily obtained.

In an alcohol solution or a mixed solution of an alcohol and water, the solubility of $M_4XA$ is very low as compared with the alkali 2-naphthoates, or dialkali 2,6-naphthalenedicarboxylates, and therefore, it is possible to separate $M_4XA$ selectively from the crude $M_4XA$.

Not only the crude $M_4XA$ separated from the reaction mixture by the water extracting method described above, but also the thermal rearrangement and/or disproportionation reaction products obtained by the method of this invention, either in the form of a solid, an aqueous solution or a suspension, can be purified by the alcohol adding method which comprises treating the crude $M_4XA$ with the aliphatic alcohol.

If the crude $M_4XA$ is in the form of an aqueous solution which is too dilute, a large quantity of the alcohol is required to precipitate $M_4XA$. Accordingly, in such a case, it is preferred to adjust the concentration of $M_4XA$ in the aqueous solution to at least 0.1% by weight, preferably at least 1% by weight.

The aliphatic alcohol used as a purifying medium in the alcohol adding method is peferably lower, especially that containing 1 to 4 carbon atoms. Examples of the especially effective alcohols are monohydric alcohols such as methanol, ethanol, n-propanol, isopropanol, and tert.-butanol, dihydric alcohols such as ethylene glycol or tetramethylene glycol, and glycol monoethers such as methyl cellosolve. Of these, the monohydric alcohols are preferred, and methanol is especially superior. These alcohols may be used either alone or as a mixture of two or more. Furthermore, they may be used as a mixture with water. Where the aliphatic alcohol is used as a mixture with water, the content of the alcohol in the mixture is at least 20% by weight, Preferably at least 30% by weight, more preferably at least 50% by weight.

$M_4XA$ and other alkali metal naphthalenetetracarboxylates are soluble in water in considerable amounts, but in alcohol, the difference in solubility between these becomes far greater than in water. Furthermore, there is a tendency that the solubilities of these in water-containing alcohols decrease with increasing proportion of the alcohol. The rate of decrease is not so remarkable with alkali metal naphthalenecarboxylates other than $M_4XA$, but is very abrupt in the case of $M_4XA$. Accordingly, pure $M_4XA$ can be selectively precipitated and separated, for example, by stirring the solid crude $M_4XA$ in alcohols or adding the alcohol gradually to an aqueous solution of the crude $M_4XA$.

The solubilities of some potassium salts in a mixture of water and methanol measured at 30°C. are shown in Table 4 below.

Table 4

| Solute | Amount (g) of solute dissolved in 100 g of a mixture of water and methanol at 30°C. Methanol concentration (wt. %) | | | | |
|---|---|---|---|---|---|
| | 0 | 40 | 60 | 80 | 100 |
| Potassium 2-naphthoate | 80 | 45 | 30 | 19 | 9.3 |
| Potassium 2,6-naphthalene-dicarboxylate | 32 | 8.5 | 3.6 | 0.88 | 0.17 |
| Tetrapotassium 1,3,5,7-naphthalenetetracarboxylate dihydrate | 45 | 9 | 1.7 | 0.13 | 0.30 |

It is seen from Table 4 that the solubility of $K_4XA$ in water is very high, but decreases abruptly with increasing concentration of methanol. On the other hand, the solubilities of the potassium 2-naphthoate and dipotassium 2,6-naphthalenedicarboxylate decrease with higher methanol concentrations but not to such a great extent as in the case of $K_4XA$. Thus, by using a mixture of methanol and water having a relatively high methanol concentration, for example, a methanol concentration of at least 30% by weight, preferably at least 50% by weight, high purity tetrapotassium 1,3,5,7-naphthalenetetracarboxylate free from potassium 2-naphthoate or dipotassium 2,6-naphthalenedicarboxylate can be advantageously separated.

The solubilities of the potassium salts of various carboxylic acids mentioned above show the same tendency also with respect to other alkali metal salts such as sodium salts, and also with respect to other alcohols.

The alcohol adding method is intended to purify the crude $M_4XA$ by utilizing the difference in solubility in the lower alcohol or its aqueous solution between $M_4XA$ and other impurities. Accordingly, various purifying means can be employed by which the impurities are dissolved in the lower alcohol or its aqueous solution and $M_4XA$ can be separated as a solid from the solution having dissolved the impurities therein. For example, there can be employed a precipitation method adding a poor solvent (for example, an alcohol) to the solution of $M_4XA$, an extracting method, a recrystallization method, or a concentrating method. Some examples of these methods are shown below.

a. A method wherein an aqueous solution of the crude $M_4XA$ is mixed with an alcohol or a water-containing alcohol to raise the alcohol concentration and thus to precipitate $M_4XA$, and the precipitate is separated.

b. When crude $M_4XA$ is obtained as a solid or a mixture of a solid and aqueous solution, the $M_4XA$ is dissolved in water, and if desired, water-insoluble impurities are removed, after which an alcohol or a water-containing alcohol is mixed with the solution to separate $M_4XA$ and separate it.

c. When the crude $M_4XA$ is obtained as a solid or a mixture of a solid and aqueous solution, it is mixed with an alcohol or a water-containing alcohol, and the mixture is fully stirred to leave $M_4XA$ as a solid and dissolve the impurities in the solvent, thereby separating $M_4XA$.

d. A method wherein the crude $M_4XA$ is dissolved in an alcohol or a mixture of an alcohol and water by heating, and the resulting solution is cooled to separate the crystallized $M_4XA$.

e. A method wherein the crude $M_4XA$ is dissolved in an alcohol and the alcohol is evaporated off from the resulting solution, to crystallize $M_4XA$ and separate it.

f. A method wherein the crude $M_4XA$ is dissolved in a mixture of an alcohol and water, components consisting mainly of water are removed by distillation to lower the water content and crystallize $M_4XA$, which is then separated.

Of these, the methods (a), (b) and (c) are preferred.

In the above purifying operation, the temperature and the amount of the medium can be determined by measuring the solubility of $M_4XA$ in the medium by simple experiments, and also can be varied by the purity of the desired $M_4XA$.

4. Addition of Alcohol-Alkali Metal Compound

This separating method corresponds to the purifying method described in paragraph (3) above which is performed in the presence of at least one alkali metal compound selected from the group consisting of hydroxides, carbonates, hydrogencarbonates, halides and sulfates of alkali metals.

According to this procedure, $M_4XA$ of higher purity can be obtained in good yields by using a lesser amount of an aliphatic alcohol than in the case of purifying crude $M_4XA$ by the alcohol adding method described in paragraph (3).

As previously stated, the solubility of $M_4XA$ in a mixture of an alcohol and water tends to decrease very abruptly with increasing alcohol content. It has now been found further that if the alkali metal compound described above is present in the alcohol or the mixture of a alcohol and water, this tendency becomes more marked, and even when the alcohol content is low, the solubility of $M_4XA$ decreases greatly.

The solubility of potassium naphthalenecarboxylate at 30°C. (amount of tetrapotassium 1,3,5,7-naphthalenetetracarboxylate dissolved in 100 g of a mixture of water and methanol at 30°C.) is shown in Table 5 below.

Table 5

| Concentration of methanol (% by weight based on the mixture of water and methanol) Solvent | Amount of $K_2CO_3$ (% by weight based on the mixture of water and methanol) Solvent | Amount of tetrapotassium salt (g) |
|---|---|---|
| 40 | 0 | 9.0 |
|  | 10 | 3.8 |
|  | 20 | 1.0 |
|  | 30 | 0.2 |
| 60 | 0 | 1.7 |
|  | 10 | 0.1 |
| 80 | 0 | 0.13 |
|  | 3 | less than 0.01 |

It is seen from Table 5 that where the alcohol content is the same, the solubility of tetrapotassium 1,3,5,7-naphthalenetetracarboxylate ($K_4XA$) becomes abruptly small with increasing amount of potassium carbonate added, and it is possible to precipitate $K_4XA$ effectively even if the concentration of methanol is relatively low.

On the other hand, it has been observed that in the absence of $M_4XA$ alkali metal naphthalenecarboxylates other than $M_4XA$ show a decreasing solubility in solvent in the presence of such an alkali metal compound. Accordingly the alkali metal naphthalenecarboxylates other than $M_4XA$ would appear to be more susceptible to precipitation by the addition of the alkali metal compound. Unexpectedly, however, it has been found that when the above alkali metal compound is added, the contents of the impurities in the purified $M_4XA$ are far smaller than in the case of not adding such an alkali metal compound. This is a very strange phenomenon, but it is presumed that since it is known that in aqueous solution, the solubility of the alkali metal salt of naphthoic acid or naphthalenedicarboxylic acid is remarkably reduced with increasing concentration of $M_4XA$, the addition of the alkali metal compound to a mixture of an alcohol and water containing a large quantity of $M_4XA$ would result in the reduction in the amount of $M_4XA$ dissolved, and therefore, the solubilities of the impurities would become all the better.

The purification of crude $M_4XA$ by the addition of the alcohol and the alkali metal compound can be carried out in the same way as set forth in paragraph (3) for the alcohol adding method, except that the alkali metal compound is present in the purifying medium composed of the alcohol or the mixture of the alcohol and water.

Examples of the alkali metal compounds that can be added are hydroxides such as potassium hydroxide or sodium hydroxide, carbonates such as potassium carbonate or sodium carbonate, hydrogencarbonates such as potassium hydrogencarbonate or sodium hydrogencarbonate, halides such as potassium chloride, potassium bromide or sodium chloride, and sulfates such as potassium sulfate or sodium sulfate. The hydroxides, carbonates and halides are especially preferred.

The amount of such an alkali metal compound to be added can be varied according to the type of the crude $M_4XA$ to be purified, the type of the medium, the temperature, the purity of the desired $M_4XA$, etc., but the optimum amount can be easily determined by measuring the solubility of $M_4XA$ through simple routine tests. Generally, when the amount of the alkali metal compound is small, the effect of adding this compound is low. When, on the other hand, it is added in an amount exceeding its solubility in the medium, it remains as a solid not dissolved in the medium, and the separation of the precipitated $K_4XA$ becomes complicated. Thus, the use of it in too great an amount is undesirable. Generally, however, the amount is 0.1 to 2 times, preferably 0.5 to 1.2 times, the saturation solubility in the medium.

5. Esterification:

The alkali metal 1,3,5,7-naphthalenetetracarboxylate produced by the process of this invention described above can be converted to free 1,3,5,7-naphthalenetetracarboxylic acid, either as such or after purification, by precipitating it with a mineral acid such as hydrochloric acid or sulfuric acid. However, because of its very low solubility in various solvents, it is not advantageous to purify the resulting 1,3,5,7-naphthalenetetracarboxylic acid to a high purity by such means as crystallization.

According to the esterification method, the crude 1,3,5,7-naphthalenetetracarboxylic acid is converted to its ester which is soluble in an organic solvent and can be crystallized from the solvent, and purified in the form of ester using the organic solvent in accordance with an extraction method, or a recrystallization method.

Crude 1,3,5,7-naphthalenetetracarboxylic acid prepared by any methods can be purified by the esterification method. For example, it may be one obtained by precipitating the thermal rearrangement and/or disproportionation reaction mixture with an acid, or one obtained by acid precipitation of an alkali metal 1,3,5,7-naphthalenetetracarboxylate separated and or purified to some extent from the above reaction mixture. If, however, the resulting crude 1,3,5,7-naphthalenetetracarboxylic acid contains too small an amount of the tetracarboxylic acid, a large quantity of solvent is required in the subsequent purifying step. Thus, generally, those containing at least 10% by weight, preferably at least 20% by weight, more preferably at least 50% by weight, of 1,3,5,7-naphthalenetetracarboxylic acid can be advantageously used.

The preferred ester of 1,3,5,7-naphthalenetetracarboxylic acid is an alkyl or alkenyl ester. Preferred alkyl or alkenyl esters are those in which the alkyl or alkenyl moiety has not more than 13 carbon atoms, especially not more than 8 carbon atoms, and most preferably is a lower alkyl or alkenyl group containing not more than 4 carbon atoms such as methyl or ethyl.

According to the esterification method, 1,3,5,7-naphthalenetetracarboxylic acid is converted to its ester, and purified by utilizing the difference in solubility in organic solvents between the ester and the other carboxylic acids such as naphthalene mono-, di-, and tri-carboxylic acids.

Preferred solvents that can be used for this purpose include, for example, aliphatic alcohols such as methanol or ethanol, aromatic hydrocarbons such as benzene or toluene, aromatic halogen compounds such as chlorobenzene or chlorotoluene, aliphatic halogen compounds such as dichloromethane or chloroform, ketones such as acetone or methylethyl ketone, esters such as methyl acetate or ethyl acetate, amide compounds such as dimethyl formamide or diethyl formamide, and glycol ethers such as methyl cellosolve and ethyl cellosolve.

The amount of the organic solvent required to substantially dissolve the crude 1,3,5,7-naphthalenetetracarboxylic acid ester varies according to the type of the solvent and the dissolving temperature. In the case of methanol, the amount is at least 5 times the weight of the ester, preferably at least 50 times and up to 2000 times, preferably up to 1,000 times, the weight of the ester. The dissolving temperature differs according to the type and amount of the medium. When the solvent used is methanol, the dissolving temperature may be not higher than the critical temperature, and the dissolution may be carried out at an elevated temperature.

According to this esterification method, the crude 1,3,5,7-naphthalenetetracarboxylic acid ester is purified by crystallization from its solution in an organic solvent. This crystallization can be performed by a conventional method, for example, by concentration and/or cooling of the solution. The extent of concentrating differs according to the type of the organic solvent and the amounts of the impurities, such as naphthalene mono-, di-, and tri-carboxylic acid esters, contained in the crude 1,3,5,7-naphthalenetetracarboxylate, but may be any extent which does not substantially worsen the purifying effect. The cooling temperature is not critical, and can be at a temperature above the freezing point of the organic solvent. Preferably, the solution may be cooled to a temperature about 20°C. The purified 1,3,5,7-naphthalenetetracarboxylate precipitated in the organic solvent is separated easily from the organic solvent by conventional solid-liquid separating techniques, such as filtration, centrifugal separation or centrifugal sedimentation. The purified 1,3,5,7-naphthalenetetracarboxylate so separated and recovered is preferably washed further with an organic solvent in order to remove any impurities that might remain there. If desired, the purified 1,3,5,7-naphthalenetetracarboxylate separated and recovered may be again subjected to crystallization.

If a solution in an organic solvent of the crude 1,3,5,7-naphthalenetetracarboxylate contains insoluble substances or is colored, the purifying effect will be further increased by performing an additional treatment such as a solid-liquid separating treatment to remove the insoluble substances and/or a decolorizing treatment using activated carbon or activated clay.

In order to form an ester of 1,3,5,7-naphthalenecarboxylic acid to be subjected to the esterification method described above, any known esterification method can be used, for example, an esterification method involving the above acid with an alcohol at an elevated temperature in the absence of a catalyst, or an esterification method comprising reacting the acid with an alcohol in the presence of a catalyst. Examples of suitable esterification catalysts are sulfuric acid, transition metals such as iron, cobalt, or nickel, metals of Group 6 B, such as molybdenum or tungsten, elements of Group 4 such as tin or lead, elements of Group 5 such as antimony or bismuth, other metals such as zinc, copper or aluminum, inorganic salts such as sulfates or hydrochlorides of these metals, or inorganic salts of calcium.

Another esterification method that can be utilized comprises converting crude 1,3,5,7-naphthalenetetracarboxylic acid to its acid halide using a halogenated sulfur compound such as thionyl chloride or thionyl bromide and a halogenated phosphorus compound such as phosphorus oxychloride, phosphorus pentachloride, phosphorus trichloride, or phosphorus oxybromide, and then reacting the acid halide with an alcohol to form an ester of the crude 1,3,5,7-naphthalenetetracarboxylic acid.

The esterification reaction mixture so obtained can be submitted to the above-described purification step as such.

When the esterification of 1,3,5,7-naphthalenetetracarboxylic acid is carried out in an alcohol, the acid is temporarily dissolved in the alcohol with the progress of the esterification reaction, and with further progress of the esterification reaction, it sometimes happens according to the amount of the alcohol that only the ester of the above acid is selectively precipitated, and the impurities such as the esters of naphthalene mono-, di-, and tricarboxylic acids remain dissolved in the alcohol. This is because the solubility of the alkyl or alkenyl ester of 1,3,5,7-naphthalenetetracarboxylic acid is lower than an alkyl ester of naphthalene mono-, di-, or tri-carboxylic acid.

When the amount of the medium is large, concentrating and/or cooling the reaction mixture results in the precipitation of a purified alkyl or alkenyl 1,3,5,7-naphthalenetetracarboxylic acid. The purified 1,3,5,7-naphthalenetetracarboxylate so precipitated can be separated and recovered by the method described above.

Therefore, this esterification method in accordance with the present invention has the advantage that an alcohol for esterification can be used as a purifying medium at the same time as the esterification of crude 1,3,5,7-naphthalenetetracarboxylic acid.

Where crude 1,3,5,7-naphthalenetetracarboxylic acid containing large quantities of impurities such as naphthalene mono-, di- and tri-carboxylic acids is used in performing the above esterification method, it is preferred to remove part of the impurities by pre-treatment. For example, the thermal rearrangement and/or disproportionation reaction product obtained by the process of this invention is dissolved in water, and the insoluble substances are removed by a solid-liquid separating technique. When the resulting liquid phase is concentrated and/or cooled, an alkali metal salt of 2,6-naphthalenedicarboxylic acid first precipitates. Thus, this alkali metal salt is separated by a solid-liquid separating technique. The filtrate obtained is further concentrated and/or cooled to precipitate an alkali metal salt of the crude 1,3,5,7-naphthalenetetracarboxylic acid. The precipitated alkali metal salt is separated from the medium by a solid-liquid separation technique to obtain an alkali metal salt of the crude 1,3,5,7-naphthalenetetracarboxylic acid having a relatively high purity as a solid, which can be subjected to the above-described esterification method.

The esterification method described above is performed not merely for the purpose of purifying XA. The 1,3,5,7-naphthalenetetracarboxylic acid ester purified by this esterification method is important as a material for producing polymeric materials, which can be formed into high molecular substances by ester-interchange.

The alkali metal salts and esters of 1,3,5,7-naphthalenetetracarboxylic acid produced and purified by the procedure described above can be used for various uses. These salts or esters can also be subjected to acid precipitation or hydrolysis to form free 1,3,5,7-naphthalenetetracarboxylic acid.

The acid precipitation of the alkali metal 1,3,5,7-naphthalenetetracarboxylates can be performed by any methods usually employed for acid precipitation of alkali metal salts of carboxylic acids.

Acid precipitation of ordinary alkali metal carboxylates is performed by dissolving the alkali carboxylates in a medium, and adding a mineral acid or organic acid to convert them to free carboxylic acids. However, where free tetracarboxylic acid is to be obtained by acid precipitation of $M_4XA$, it is comparatively difficult to convert all of it into a free acid, and even when an excess of acid is present, the acid precipitation tends to stop at the stage of a monoalkali metal salt. This is presumably because the solubility of the monoalkali salt in the medium is very low, and the reaction of the monoalkali salt separated as solid hardly proceeds to form XA. In the case of acid precipitation of $M_4XA$, the following expedients should be employed as compared with the ordinary acid precipitation, in order to allow the reaction to proceed fully.

1. The medium is used in an amount preferably as great as more than 20 times the amount of $M_4XA$.
2. The reaction is performed at a high temperature of, for example, more than 60°C.
3. The mineral acid is used in a large excess, for example, more than 2 times the theoretical amount.

4. A combination of two or three of these procedures (1) to (3).

Since the 1,3,5,7-naphthalenetetracarboxylic acid rendered free by such a method has very low solubility, it can be easily separated by precipitating it as a slurry, and subjecting the slurry to solid-liquid separation.

The hydrolysis (saponification) of the esters of 1,3,5,7-naphthalenetetracarboxylic acid can also be performed by any desired known methods. For example, the esters are saponified in an alcohol or an alkaline aqueous medium such as sodium hydroxide or potassium hydroxide to convert them to alkali salts, and then subjecting the alkali salts to acid precipitation in the manner described above. Or the esters can be hydrolyzed with an acidic aqueous medium such as hydrochloric acid or sulfuric acid with heating, if desired. The free 1,3,5,7-naphthalenetetracarboxylic acid so formed can be easily separated from the reaction medium by a solid-liquid separating technique.

The tetraalkali metal 1,3,5,7-naphthalenetetracarboxylates ($M_4XA$) obtained by the present invention in the above-described manner exhibit unique reactivity with acids, and it has been found surprisingly that when $M_4XA$ is brought into contact with a mineral acid or organic acid in an aqueous medium, A 3,7-dialkali metal 1,3,5,7-naphthalenetetracarboxylate ($M_2H_2XA$) having superior symmetry is formed selectively.

According to another aspect of this invention, therefore, there is provided a process for preparing 3,7-dialkali metal 1,3,5,7-naphthalenetetracarboxylates expressed by the following formula

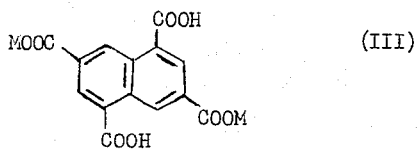

wherein M is an alkai metal, preferably potassium or sodium, which comprises bringing a tetraalkali metal 1,3,5,7-naphthalene-tetracarboxylate expressed by the following formula

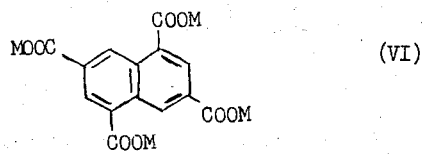

wherein M is the same as defined above, into contact with a mineral acid or organic acid in an aqeuous medium.

The aqueous medium used in this reaction is water or a mixture of water with a water-miscible inert organic solvent, for example, lower aliphatic alcohols such as methanol or ethanol, lower aliphatic ketones such as acetone or methyl ethyl ketone, or cyclic ethers such as dioxane or tetrahydrofuran.

Where the mixture of water and the water-miscible organic solvent is used, it preferably has a water content of at least 10%, especially at least 20%, because the solubility of $M_4XA$ generally decreases with decreasing water content of the mixed medium and the progress of the reaction becomes increasingly difficult.

Even when $M_4XA$ is present in an amount exceeding its solubility in the aqueous medium, treatment of it with acid for sufficient periods of time can result in the formation of $M_2H_2XA$. Generally, the higher the concentration of $M_4XA$ in the aqueous medium, the easier it is to obtain the crystals of $M_2H_2XA$. When the concentration of $M_4XA$ is low, free 1,3,5,7-naphthalenetetracarboxylic acid or its monoalkali metal salts tend to be formed as by-products.

The concentration of $M_4XA$ in the aqueous medium is not critical, but can be varied over a wide range according to such factors as the reaction conditions, or the type or concentration of the acid used. When the aqueous medium is water, the suitable concentration of $M_4XA$ is generally at least 2% by weight, preferably at least 5% by weight. When the mixed aqueous medium is used, the concentration of $M_4XA$ may be lower than in the case of using water as medium.

Suitable mineral acids that can be used for this purpose are strong inorganic acids such as hydrochloric acid, sulfuric acid or nitric acid. The amount of the mineral acid is generally not more than 2.5 equivalents, suitably 0.5 to 2.2 equivalents, per mol of $M_4XA$ since the use of a large excess of the mineral acid tends to cause undesirable side reactions. When $M_4XA$ is present in a relatively high concentration in the aqueous medium, even the use of a small amount of a mineral acid, for example, less than 1 equivalent per mol of $M_4XA$, can lead to the selective formation of $M_2H_2XA$.

The use of organic acids having too weak acidity should be avoided. Usually, those having a pKa value of not more than 5.4 are advantageously used. Examples of suitable organic acids are aliphatic carboxylic acids such as formic acid, acetic acid, propionic acid, caproic acid, acetoacetic acid, glutaric acid, oxalic acid, or chloroacetic acid, aromatic carboxylic acids such as benzoic acid, phthalic acid or chlorobenzoic acid, and organic sulfonic acids such as benzenesulfonic acid. Derivatives of acids easily convertible to free acids in aqueous medium, such as acetic anhydride or phthalic anhydride, can equally be used.

When using such an organic acid, it can be used in a larger amount since unlike the case of using a mineral acid, the proportion of $M_2H_2XA$ that is decomposed is small even if the organic acid is used in an amount of more than 2 equivalents per mol of $M_4XA$. Generally, the organic acid is used preferably in an amount of 0.5 to 3.5 equivalents per mol of $M_4XA$.

By the process described above, $M_2H_2XA$ can be selectively obtained in accordance with the following equation (2).

$$M_4XA + 2HA \rightarrow M_2H_2XA + 2MA \qquad (2)$$

wherein HA represents an acid, and MA represents an alkali metal salt of the acid.

The $M_2H_4XA$ so precipitated is a relatively unstable substance, and when a mineral acid or a certain organic acid is present in large excess, it often reacts further with the acid to form a monoalkali metal 1,3,5,7-naphthalenecarboxylate (to be abbreviated as $MH_3XA$) or free 1,3,5,7-naphthalene tetracarboxylic acid (to be abbreviated as $H_4XA$) as shown in the following equations (3) and (4).

$$M_2H_2XA + HA \rightarrow MH_3XA + MA \qquad (3)$$

$$MH_3XA + HA \rightarrow H_4XA + MA \qquad (4)$$

Accordingly, in order to obtain $M_2H_2XA$ selectively, it is very desirable to use the mineral acid or organic acid in the above-specified amount.

The precipitated $M_2H_2XA$ crystals are also unstable to cold or hot water, and in the presence of a large quantity of water, would be partly converted to a monoalkali metal 1,3,5,7-naphthalenedicarboxylate ($MH_3XA$) and $M_4XA$ in accordance with the following equation (5).

$$3M_2H_2XA \rightarrow 2MH_3XA + M_4XA \qquad (5)$$

Accordingly, when it is desired to precipitate $M_2H_2XA$ by treating a relatively dilute solution of $M_4XA$ with an acid, it is preferred to use a mixture of water with the organic solvent.

When $M_4XA$ is brought into contact with the acid in the aqueous medium, it is preferred to add the mineral acid or organic acid gradually to an aqueous medium solution of $M_4XA$ with thorough stirring so that the acid concentration does not increase locally.

The reaction proceeds fully even at room temperature. However, when a solution of $M_4XA$ in a high concentration is subjected to acid precipitation, the concentration of the slurry increases at low temperatures and stirring tends to become difficult since the crystal particles of $M_2H_2XA$ formed are fine. In such a case it is preferred to elevate the reaction temperature, for example, to a temperature of 40° to 80°C., since it results in the formation of $M_2H_2XA$ of large particle diameter and in better flow-ability of the slurry.

The above procedure can lead to the precipitation of $M_2H_2XA$ as crystals in the aqueous medium. The crystals are evaporated to dryness, or separated by conventional solid-liquid separating techniques, before using in the various applications described above.

We have further found that when $H_4XA$ and/or $MH_3XA$ is reacted with $M_4XA$, $M_2H_2XA$ of the formula (III) having good symmetry can be obtained in accordance with the following equations (6) and (7).

$$H_4XA + M_4XA \rightarrow 2M_2H_2XA \qquad (6)$$

$$2MH_3XA + M_4XA \rightarrow 3M_2H_2XA \qquad (7)$$

Generally, this reaction can be performed in an aqueous medium, and the aqueous medium to be used may be the same as that used in acid treatment of $M_4XA$. This reaction is a disproporationation reaction between $H_4XA$ and/or $MH_3XA$ which are almost insoluble in such an aqueous medium and $M_4XA$ which is relatively well soluble in the aqueous medium. $H_4XA$ and $MH_3XA$ to be reacted with $M_4XA$ may be used singly or as a mixture of the two.

The reaction generally proceeds more easily with higher concentration of $M_4XA$ in the aqueous medium. Usually, the concentration of $M_4XA$ is at least 2% by weight, or at least 5% by weight.

The ratio of $H_4XA$ and/or $MH_3XA$ to $M_4XA$ is not critical, but is preferably around the theoretical value in the reaction equations (6) and (7). Even if the ratio is different from the theoretical ratio, it is possible to form $M_2H_2XA$. If in this case, the amount of $M_4XA$ is smaller than $H_4XA$ and/or $MH_3XA$, solid $M_2H_2$ and solid unreacted $H_4XA$ and/or $MH_3XA$ are present in the reaction product. Thus, when it is desired to avoid the mixing of the unreacted $H_4XA$ and/or $MH_3XA$ in the resulting $M_2H_2XA$, the water-soluble $M_4XA$ is preferably used in an amount larger than the theoretical value. If care is taken so that $M_4XA$ is not used in such a large amount as to cause it to remain as an undissolved solid, the unreacted $M_4XA_4$ is generally separated easily by solid-liquid separation techniques from the resulting solid $M_2H_2XA$.

Generally, the rate of reaction is higher at a higher temperature, but at the same time, the rate of decomposition also increases. This may sometimes lead to a reduction in the purity of the $M_2H_2XA$ separated. In such a case, the reaction is first performed at an elevated temperature in order to increase the rate of reaction, and after a greater part of the reaction has been effected, the reaction system is cooled, and the reaction is completed at a low temperature. This procedure results in the formation of $M_2H_2XA$ crystals having a large particle size in a high yield. This procedure is especially preferred since the $M_2H_2XA$ crystals can be easily separated.

The first-stage of the above reaction can be performed at a temperature of at least 50°C., preferably at least 80°C., or can also be carried out at a temperature of at least 100°C. at an elevated pressure. It is desirable that the second-stage of the reaction be completed at a temperature of not more than 80°C., preferably not more than 60°C., and then the resulting crystals be separated. This procedure makes it possible to obtain $M_2H_2XA$ of large particle diameter and of high purity within short periods of time.

The $M_2H_2XA$ is thus obtained as a solid in an aqeuous medium. Preferably, $M_2H_2XA$ is washed with a small amount of cold water or an organic solvent of the type described above after separation from the medium.

$M_2H_2XA$ so obtained can be converted to a dialkali metal 2,6-naphthalenedicarboxylate useful as a material for producing polyesters, by heating at a temperature of, for example, 300° to 550°C., preferably in an atmosphere of an inert gas, and therefore, it is a commercially interesting compound.

The following Examples further illustrate the present invention.

FIG. 1 represents the Infrared Absorption Spectrum of tetramethyl 1,3,5,7-naphthalenetetracarboxylate from Example 1;

FIG. 2 represents the Nuclear Magnetic Resonance Absorption Spectrum of tetramethyl 1,3,5,7-naphthalenetetracarboxylate from Example 1;

FIG. 3 represents the Infrared Absorption Spectrum of 1,3,5,7-naphthalenetetracarboxylic acid from Example 1;

FIG. 5 represents the Infrared Absorption Spectrum of the dihydrate of tetrapotassium 1,3,5,7-naphthalenetetracarboxylate from Example 7;

FIG. 6 represents the Infrared Absorption Spectrum of dipotassium 1,3,5,7-naphthalenetetracarboxylate from Example 18.

Figure 4:
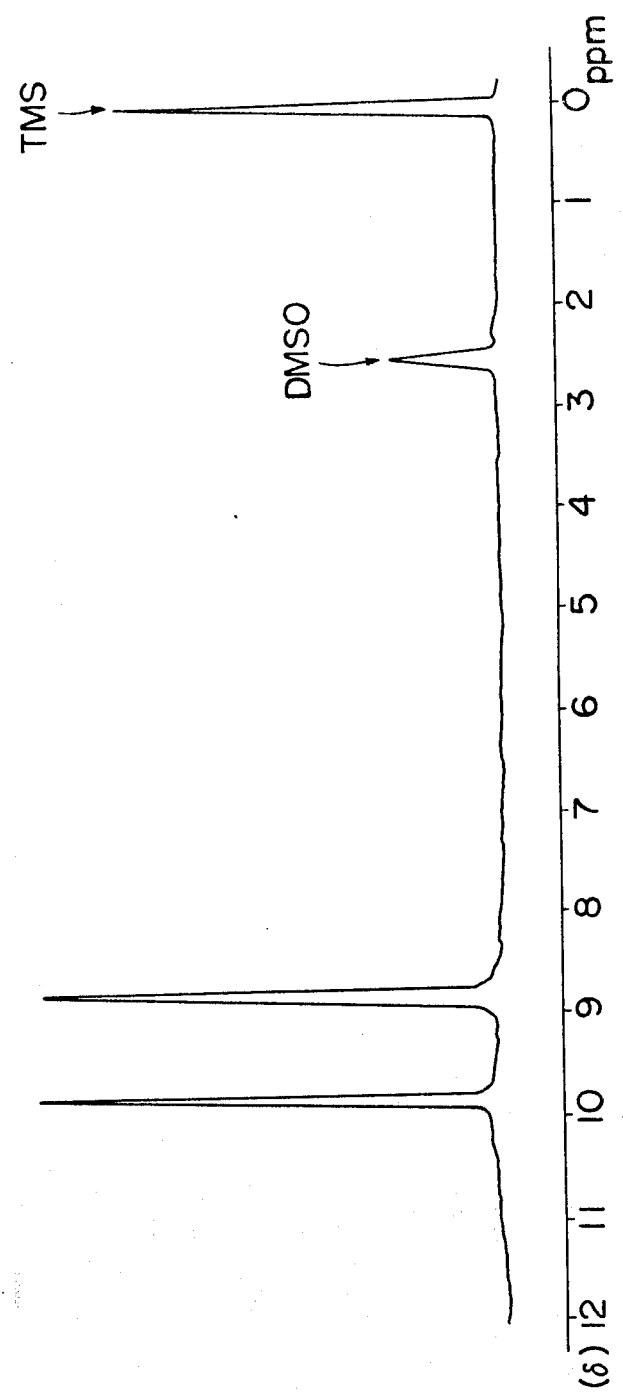
FIG. 4 represents the Nuclear Magnetic Resonance Absorption Spectrum of 1,3,5,7-naphthalenetetracarboxylic acid from Example 1.

Unless otherwise specified, all percentages and parts are on the weight basis.

EXAMPLE 1

A mixture consisting of 30% of potassium 1-naphthoate and 70% of potassium 2-naphthoate was dissolved in water, and 4 mol% of zinc naphthoate, 3 mol% of potassium chloride, and 5 mol% of potassium carbonate, all based on the total amount of the potassium 1- and 2-naphthoates, were added. With stirring, the mixture was concentrated to dryness while evaporating off water, and further dried for at least 2 days at 110° to 130°C., followed by pulverization. 100 Parts of the resulting starting mixture was charged in a stainless steel reactor equipped with a stirrer, and after purging it with carbon dioxide gas, carbon dioxide gas was introduced into the stainless steel reactor to a pressure of 30 Kg/cm².

Then, the reaction temperature was raised to 450°C. at a rate of 5°C./minute, and the reaction mixture was maintained at this temperature to allow it to react for 5 hours. During the reaction, the carbon dioxide gas was purged out of the reactor so as to maintain the pressure of the carbon dioxide gas in the reactor always at 30 Kg/cm².

After the reaction, 70 parts of the reaction product was boiled for 0.5 hour together with 200 parts of water and was hot filtered to remove the insoluble substances. To the resulting filtrate was added 6N hydrochloric acid to perform acid precipitation and to adjust the pH to not more than 2. The mixture was then filtered, and dried to form 40 parts of a cake.

A reactor equipped with a stirrer was charged with 40 parts of the dried cake, 200 parts of methanol, and 10 parts of sulfuric acid, and they were allowed to react with stirring for 8 hours at 150°C.

The reaction product was poured into 500 parts of water, and the resulting precipitate was filtered, washed with water, and dried.

The cake as dried was vacuum distilled at a pressure of 15 mmHg, whereupon methyl naphthoate was first distilled off, and then dimethyl-2,6-naphthalenedicarboxylate. (The dimethyl 2,6-naphthalenedicarboxylate has a boiling point of 215°C./15 mmHg.)

The high boiling substances remaining after the distillation off of the dimethyl naphthalenedicarboxylate were added to 100 parts of dimethyl formamide to perform recrystallization thereby forming 3.5 parts of crystals.

The crystals obtained had a melting point of 250° to 251°C., and were a pure substance having the following properties:

1. Saponification value: 627 KOH mg/g (623 KOH mg/g as tetramethyl naphthalenetetracarboxylate)

2. Elemental analysis:
C: 59.94%, H: 4.27%
C: 60.00%, H: 4.48% (calculated as tetramethyl naphthalenetetracarboxylate)

3. Infrared absorption spectrum:
Shown in FIG. 1 of the attached drawings.

4. The resulting crystals were dissolved in chloroform, and analyzed by gas-chromatography under the following conditions.

| Column | 2m stainless column |
|---|---|
| Filler | OV - 17 |
| Column temperature | 250°C. |
| Carrier gas (nitrogen) | 20 cc/mm |

The time during which this substance was subjected to gas-chromatography was 33 minutes. The peak position corresponds to that of tetramethyl 1,4,5,8-naphthalenetetracarboxylate synthesized separately and subjected to gas-chromatography for the same period of time.

5. Nuclear magnetic resonance absorption spectrum: (solvent: chloroform-d₁)

Shown in FIG. 2 of the accompanying drawings. The following are noted from FIG. 2.

a. Methyl proton (—COOCH₃)/nuclear proton

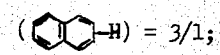

this corresponds with tetramethyl naphthalenetetracarboxylate b. Chemical shifts of the protons (delta value)

| | |
|---|---|
| 4.05 singlet | proton number 6 |
| 4.03 singlet | proton number 6 |
| Nuclear proton | |
| 8.83 singlet | proton number 2 |
| 9.85 singlet | proton number 2 | c. Calculation of the chemical shifts led to the determination that the substituting positions of —COOCH₃ are 1,3,5 and 7.

The various properties determined as above led to the confirmation that this substance is tetramethyl 1,3,5,7-naphthalenetetracarboxylate.

This substance is a new substance not known heretofore, and neither its existence nor a method for its synthesis have been known prior to this invention.

When the tetramethyl 1,3,5,7-naphthalenetetracarboxylate was hydrolyzed with alcoholic potassium hydroxide and then treated with hydrochloric acid, 2.8 parts of 1,3,5,7-naphthalenetetracarboxylic acid was obtained. The resulting 1,3,5,7-naphthalenetetracarboxylic acid had the following properties.

1. Melting point: above 300°C. (decomposed at high temperatures)
2. Acid value: 738 KOH mg/g (theoretical value, 737.8 KOH mg/g)
3. Elemental analysis value:

C: 55.24% (calculated, 55.28%).

H: 2.54% (calculated 2.65%).

4. Infrared absorption spectrum:
As shown in FIG. 3 of the attached drawings.
5. Nuclear magnetic resonance absorption spectrum:
As shown in FIG. 4 of the attached drawings.

Measuring conditions:

Solvent, dimethyl sulfoxide-d₆ (DMSO-d₆)
Temperature, 80°C.
Magnetic field, 100 MHz
6. Insoluble in water, alcohols, ethers, benzene.

EXAMPLE 2

To an aqueous solution of potassium 2-naphthoate was added 4 mol%, based on the potassium salt, of cadmium iodide. With stirring, the mixture was concentrated to dryness, and dried for at least 2 days at 110° to 130°C., followed by pulverization. 100 Parts of the pulverized mixture was charged into a reactor equipped with a stirrer, and after purging with carbon dioxide gas, the reactor was charged with carbon dioxide gas to a pressure of 40 Kg/cm$^2$. Then, in the same way as in Example 1, the reactor was heated up to 400°C. The reaction mixture was maintained at this temperature and allowed to react for 4 hours. When 73 parts of the resulting reaction product was treated in the same way as in Example 1, 1.5 parts of 1,3,5,7-naphthalenetetracarboxylic acid was obtained.

EXAMPLE 3

To an aqueous solution of dipotassium 1,8-naphthalenedicarboxylate were added 4 mol% of zinc chloride and 5 mol% of potassium carbonate, both based on the dipotassium 1,8-naphthalenedicarboxylate. With stirring, the mixture was concentrated to dryness, and dried for at least 2 days at 110° to 130°C., followed by pulverization. 100 Parts of the resulting starting mixture was placed in a reactor equipped with a stirrer, and after purging with carbon dioxide gas, the reactor was charged with carbon dioxide gas to a pressure of 30 Kg/cm$^2$.

Then, the reactor was heated to 450°C. in the same way as in Example 1, and the reaction mixture was maintained at this temperature and reacted for 5 hours. The resulting reacton product was treated in the same way as in Example 1 to form 1.9 parts of 1,3,5,7-naphthalenetetracarboxylic acid.

EXAMPLE 4

To an aqueous solution of tripotassium 2,3,6-naphthalenetricarboxylate was added 4 mol%, based on the 2,3,-naphthalenetricarboxylate, of zinc iodide, and the starting mixture was prepared in the same way as in Example 1. A reactor equipped with a stirrer was charged with 100 parts of the starting mixture, and after purging with carbon dioxide gas, filled with carbon dioxide gas to a pressure of 30 Kg/cm$^2$.

The reaction product so obtained was treated in the same way as in Example 1 to form 3.0 parts of 1,3,5,7-naphthalenetetracarboxylic acid.

EXAMPLE 5

A mixture consisting of 27% of potassium 1-naphthoate and 63% of potassium 2-naphthoate, and 10%, based on the total amount of the above two potassium salts, of tetrapotassium 1,3,5,7-naphthalenetetracarboxylate were dissolved in water, and 4 mol% of zinc naphthoate, 5 mol% of potassium carbonate and 3 mol% of potassium chloride, all based on the total amount of the above three potassium salts, were added. With stirring, the mixture was concentrated to dryness while evaporating off water, and dried for at least 2 days at 110° to 130°C.

A stainless steel reactor provided with a stirrer was charged with 100 parts of the resulting starting mixture, and after purging with carbon dioxide gas, filled with carbon dioxide gas to a pressure of 30 Kg/cm$^2$. Then, the temperature of the wall of the reactor was raised to 450°C. at a rate of 5°C./min., and the reaction mixture was maintained at this temperature and allowed to react for 5 hours. During the reaction, the excess carbon dioxide gas was purged out of the reactor so as to maintain the pressure of the carbon dioxide always at 30 Kg/cm$^2$.

After the reaction, 72 parts of the reaction product obtained was treated in the same way as in Example 1 to form 11.4 parts of 1,3,5,7-naphthalenetetracarboxylic acid.

EXAMPLE 6

A mixture consisting of 85% of potassium 2-naphthoate and 15% of tetrapotassium 1,3,5,7-naphthalenetetracarboxylate was dissolved in water, and 4 mol%, based on the total amount of the above two potassium salts, of cadmium iodide was added. With stirring, the mixture was concentrated to dryness, and pulverized.

A reactor equipped with a stirrer was charged with 100 parts of the pulverized mixture, and after purging with carbon dioxide gas, filled with carbon dioxide gas to a pressure of 40 Kg/cm$^2$. Then, in the same way as in Example 1, the reactor was heated to 400°C., and the reaction mixture was maintained at this temperature and allowed to react for 4 hours.

When 74 parts of the reaction product so obtained was in the same way as in Example 1, 14.8 parts of 1,3,5,7-naphthalenetetracarboxylic acid was obtained.

EXAMPLE 7

Under the same rearrangement reaction conditions as in Example 5, mixed potassium naphthoates were thermally rearranged. The resulting rearranged product was dissolved in 3 times its weight of water, and after removing the insoluble substances, the filtrate was concentrated. Dipotassium 2,6-naphthalenedicarboxylate that first precipitated was separated, and the mother liquor was again concentrated. After cooling, the precipitate was separated to form water-containing crude tetrapotassium 1,3,5,7-naphthalenetetracarboxylate in the crude form having the composition shown in Table 6 below.

Table 6

| Compound | Composition (% by weight) |
|---|---|
| Tetrapotassium 1,3,5,7-naphthalenetetracarboxylate | 55.3 |
| Dipotassium 2,6-naphthalene-dicarboxylate | 4.1 |
| Other dipotassium naphthalene-dicarboxylates | 1.2 |
| Potassium 2-naphthoate | 5.5 |
| Potassium 1-naphthoate | 0.4 |
| Tripotassium naphthalenetricarboxylate | 2.2 |
| Other compounds | 2.1 |
| Water | 29.2 |

Ten parts of the crude tetrapotassium 1,3,5,7-naphthalenetetracarboxylate having the above composition was dissolved in 20 parts of water, and then 80 parts of methanol was added. The solution was maintained at 30°C. and stirred for 30 minutes. The solution was then filtered. The cake was washed with a small amount of methanol, and then sufficiently dried in a dryer held internally at 150°C. to form 5.5 parts of purified tetrapotassium 1,3,5,7-naphthalenetetracarboxylate. The resulting purified product had the following physical properties.

1. Melting point: above 300°C. (even when the product was heated to near 450°C., almost no change occurred, but the product was stable)
2. Elemental analysis values:

C: 36.78% (calculated, 36.82%).

H: 0.90% (calculated, 0.88%).

3. K content determined by an atomic flame absorption method:

34.07% (calculated, 34.26%).

4. Readily soluble in water, and slightly soluble in methanol. When the product is recrystallized from water, a dihydrate containing two molecules of water of crystallization is obtained.
5. Infrared absorption spectrum: The infrared absorption spectrum of the dihyrate is shown in FIG. 5 of the accompanying drawings.
6. When a part of the resulting tetrapotassium 1,3,5,7-naphthalenetetracarboxylate was dissolved in water, and treated with hydrochloric acid. The precipitated product was converted into a methyl ester, and the ester was analyzed by gas-chromatography for impurities. No impurity other than small amounts of tricarboxylic acids was detected.

EXAMPLE 8

Ten parts of water-containing tetrapotassium 1,3,5,7-naphthalenetetracarboxylate in the crude form as shown in Table 2 of Example 7 was added to 60 parts of water-containing methanol having a methanol content of 60%, and the mixture was maintained at 25°C. and stirred for 30 minutes. The mixture was then filtered. The resulting cake was washed with a small amount of water-containing methanol having a methanol content of 60%, and dried to form 5.4 parts of purified tetrapotassium 1,3,5,7-naphthalenetetracarboxylate having a purity of 99%.

EXAMPLE 9

Water-containing crude tetrapotassium 1,3,5,7-naphthalenetetracarboxylic acid was treated under the same conditions as in Example 8 using 60 parts of water-containing ethanol having an ethanol content of 60% instead of the water-containing methanol. There was obtained 5.4 parts of purified tetrapotassium 1,3,5,7-naphthalenetetracarboxylate having a purity of more than 99%.

EXAMPLE 10

Ten parts of water-containing crude tetrapotassium 1,3,5,7-naphthalenetetracarboxylate as shown in Table 2 of Example 7 was dissolved in 100 parts of a mixed solvent consisting of 60 parts of water and 40 parts of methyl cellosolve. The solution was then distilled to distill off 40.2 parts of the water and 5.2 parts of the methyl cellosolve. The residue was cooled, and the resulting precipitate was separated by filtration. The cake was washed with a small amount of methyl cellosolve, and dried to form purified tetrapotassium 1,3,5,7-naphthalenetetracarboxylate having a purity of 98.4%.

EXAMPLE 11

Ten parts of water-containing crude tetrapotassium 1,3,5,7-naphthalenetetracarboxylate shown in Table 2 of Example 7 was dissolved in 20 parts of water, and 8 parts of potassium carbonate was added, followed by further addition of 20 parts of methanol. The solution was maintained at 30°C., and stirred for 30 minutes. The solution was subjected to a centrifugal separator. The cake separated was washed with a small amount of methanol, and then dried for one day with a dryer held internally at 150°C. to form 5.5 parts of purified tetrapotassium 1,3,5,7-naphthalenetetracarboxylate.

A part of the resulting tetrapotassium 1,3,5,7-naphthalenetetracarboxylate was dissolved in water, and treated with hydrochloric acid. The precipitated product was converted into a methyl ester, and the ester was subjected to gas-chromatography. Only 0.4 mol% of naphthalenetricarboxylic acids were detected, and no other impurity was observed.

EXAMPLE 12

To a mixture consisting of 30% of potassium 1-naphthoate and 70% of potassium 2-naphthoate were added 10% of tetrapotassium 1,3,5,7-naphthalenetetracarboxylate, 5 mol% of zinc carbonate, 5 mol% of potassium carbonate and 3 mol% of potassium carbonate, all based on the total amount of the potassium 1- and 2-naphthoates. 100 Parts of the resulting mixture was heated at 440°C. for 5 hours in an atmosphere of carbon dioxide gas held at 30 Kg/cm$^2$, to form 70 parts of a reaction product containing 12 parts of tetrapotassium 1,3,5,7-naphthalenetetracarboxylate. The product was dissolved in 400 parts of warm water, and the solution was stirred for 1 hour. Then, 1 part of activated carbon was added, and the mixture was further stirred for 1 hour, followed by filtration to remove 8 parts of the insoluble substances from the reaction system. Then, 70 parts of a 10% aqueous solution of potassium carbonate was added, and the mixture was concentrated by an evaporating device equipped with a stirrer. When the total K ion concentration in the concentrated mother liquor reached 8.7 g-ion/1000 g-$H_2O$, the concentrating of the mixture was stopped. At this time, the $K_2CO_3$ concentration in the mother liquor was 5.7 g-ion/1000 g-$H_2O$ calculated as K ions.

The slurry obtained was filtered to obtain 42.6 parts of cake (A) composed mainly of dipotassium 2,6-naphthalenedicarboxylate and 62.9 parts of a filtrate (B). To the resulting filtrate (B) was added 5 parts of solid potassium carbonate, and with stirring, the mixture was cooled to 22.5°C. The resulting precipitate was filtered to form 11.6 parts of cake (C). The purity of tetrapotassium 1,3,5,7-naphthalenetetracarboxylate in the cake (C) was 98.0%.

EXAMPLE 13

The same starting mixture as used in the rearrangement reaction in Example 12 was reacted under the same conditions as in Example 12 to form 70 parts of a reaction product containing 12 parts of tetrapotassium 1,3,5,7-naphthalenetetracarboxylate. The product was dissolved in warm water in the same way as in Example 12, and then treated with activated carbon to remove the insoluble substances. 70 Parts of a 10% aqueous solution of potassium carbonate was added, and the mixture was concentrated by an evaporator equipped with a stirrer. When the $K_2CO_3$ concentration of the concentrated mother liquor reached 3.78 g-ion/1000 g-$H_2O$ calculated as a potassium ion, the concentration of the mixture was stopped. At this time, the total K ion concentration of the mother liquor was 6.1 g-ion/1000 g-H₂O.

The slurry was filtered, and the resulting filtrate was cooled to 25°C. The precipitate formed was filtered to form 14.3 parts of a cake. The purity of tetrapotassium 1,3,5,7-naphthalenetetracarboxylate in the cake was 79.1%.

EXAMPLE 14

Crude tetrapotassium 1,3,5,7-naphthalenetetracarboxylate obtained in Example 13 was again dissolved in water, and the solution was acidified with hydrochloric acid to an acidity lower than pH 1 to form free crude 1,3,5,7-naphthalenetetracarboxylic acid. The product was separated and dried to form crude 1,3,5,7-naphthalenetetracarboxylic acid as shown in Table 7.

Table 7

| Compound | Composition (wt. %) |
| --- | --- |
| 1,3,5,7-naphthalenetetracarboxylic acid | 80.2 |
| Naphthalenemonocarboxylic acids | 9.8 |
| Naphthalenedicarboxylic acids | 6.8 |
| Naphthalenetricarboxylic acids | 3.2 |

A stainless steel stirring vessel was charged with 7 parts of the crude 1,3,5,7-naphthalenetetracarboxylic acid having the composition shown in Table 7, 7 parts of sulfuric acid, 140 parts of methanol, and 3 parts of copper sulfate, and the mixture was maintained at 120°C. for 5 hours under the autogeneous pressure of the methanol. The reaction mixture was cooled to 60°C., and filtered. The crystals precipitated were separated and recovered, washed twice with 24 parts of methanol, and dried at 100°C. to form 6.4 parts of purified tetramethyl 1,3,5,7-naphthalenetetracarboxylate. Gas-chromatographic analysis showed that the product contained 0.7% of trimethyl naphthalenetricarboxylate, but methyl naphthalenemonocarboxylates and dimethyl naphthalenedicarboxylates were not observed.

The recovered tetramethyl 1,3,5,7-naphthalenetetracarboxylate (6.3 parts) was heated together with 140 parts of methanol to 140°C. at the autogeneous pressure of methanol, and then cooled to 30°C. The precipitate was separated and dried to form 6.0 parts of crystals having a melting point of 250.0° to 251.0°C.

Gas-chromatographic analysis showed that in this purified tetramethyl 1,3,5,7-naphthalenetetracarboxylate any methyl esters of naphthalene mono-, di-, or tri-carboxylic acids were not observed.

EXAMPLE 15

Five parts of the same crude 1,3,5,7-naphthalenetetracarboxylic acid as shown in the Table 3 in Example 14 was suspended in 50 parts of thionyl chloride, and the suspension was heated under reflux for 48 hours. After the reaction, the excess thionyl chloride was distilled out. To the residue was added 50 parts of anhydrous ethyl ether, and with stirring, 10 parts of n-butanol was gradually added.

After the addition of n-butanol, the reaction product was heated for 24 hours under reflux with stirring. After the reaction, low boiling substances having a boiling point of not more than 140°C. were distilled off. The residue was heated to the boiling point at atmospheric pressure after addition of 15 parts of ethyl acetate and 20 parts of methanol. After being stirred for 30 minutes, the mixture was cooled to room temperature. The precipitate was filtered, and collected to obtain 3.6 parts of white needle-like crystals.

The crystals obtained showed the following properties, and were found to be substantially pure tetra-n-butyl 1,3,5,7-naphthalenetetracarboxylate.

1. Melting point: 59.2° to 60.0°C.
2. Saponification value: 427 KOH mg/g (Calculated 425).
3. Elemental analysis values:

C: 68.22% (calculated, 68.16%).

H: 7.48% (calculated, 7.63%).

4. Infrared absorption spectrum:

Characteristic spectrum
2950 cm$^{-1}$ ($\nu$C—H)
1720 cm$^{-1}$ ($\nu$C=O)
1460 cm$^{-1}$ ($\nu$C—H)
1250 cm$^{-1}$ ($\nu$C—O)
765 cm$^{-1}$ ($\delta$C—H)

5. Nuclear magnetic resonance absorption spectrum:
Chemical shift (delta value)
Nuclear proton
9.65 (singlet proton number 2)
8.65 (singlet proton number 2)
Methylene proton
4.51 (triplet proton number 4)
4.43 (triplet proton number 4)
1.83 (multiplet proton number 8)
1.56 (multiplet proton number 8)
Methyl proton
1.03 (triplet proton number 12)
Measuring conditions:-
Solvent: dimethyl sulfoxide-d₆
Temperature: 80°C.
Magnetic field: 100 MHz 6. Readily soluble in hot ethanol, ether, and chloroform.

EXAMPLE 16

A reactor was charged with 18 parts of tetramethyl 1,3,5,7-naphthalenetetracarboxylate obtained in the same way as in Example 14, 186 parts of n-dodecyl alcohol, and 0.18 part of calcium acetate monohydrate. While distilling off the metanol generated, the reaction mixture was boiled for 15 hours at the boiling point of the n-dodecyl alcohol at atmospheric pressure (245° to 255°C.) The reaction mixture was cooled to 40°C., and the insoluble substances were separated by filtration. Addition of 800 parts of methanol resulted in the separation of a brown heavy liquid layer, which was then separated. Acetone (200 parts) was added to 24 parts of the resulting brown heavy liquid layer, and the mixture was stirred for 30 minutes at 15°C. The coloring components were extracted into the acetone layer, and light yellow crystals were precipitated.

The crystals were recrystallized from 50 parts of acetone to form 14 parts of white crystals. The resulting crystals exhibited the following physical properties, and were found to be a substantially pure tetra-n-dodecyl 1,3,5,7-naphthalenetetracarboxylate.

1. Melting point: 65.0° – 66.0°C.
2. Saponification value: 232 (Calculated 230)
3. Elemental analysis values:

C: 76.09% (calculated, 76.18%)

H: 10.56% (calculated, 10.72%)

4. Infrared absorption spectrum:

Characteristic spectrum
2940 cm$^{-1}$ ($\nu$C—H)
2860 cm$^{-1}$ ($\nu$C—H)

-continued
1730 cm⁻¹ ($\nu_{C=O}$)
1473 cm⁻¹ ($\nu$C—H)
1270 cm⁻¹ ($\nu$C—O)
770 cm⁻¹ ($\delta$C—H)
720 cm⁻¹ ($\delta$C—H)

5. Nuclear magnetic resonance absorption spectrum:
    Chemical shift (delta value)
    Nuclear proton
        9.80 (singlet proton number 2)
        8.78 (singlet proton number 2)
    Methylene proton
        4.49 (triplet proton number 4)
        4.44 (triplet proton number 4)
        1.90 (multiplet proton number 8)
        1.28 (multiplet proton number 72)
    Methyl proton
        0.88 (triplet proton number 12)
    Measuring conditions:
        Solvent:        Chroloform-d₁
        Temperature:    18°C
        Magnetic field: 100 MHz
6. Readily soluble in chloroform, benzene, acetone, ether.

EXAMPLE 17

4.7 parts of purified tetrapotassium 1,3,5,7-naphthalenetetracarboxylate obtained in the same way as in Example 7 was dissolved in 200 parts of water. The solution was maintained at 30°C. with stirring, and 11 parts of 6N hydrochloric acid was added gradually. After the addition, the stirring was continued further for 10 minutes. The resulting slurry was filtered, and the cake was washed with 100 parts of water and sufficiently drid at 110°C. to form 3.8 parts of fine white crystals.

The crystals showed the following physical properties and were found to be a substantially pure monopotassium 1,3,5,7-naphthalenetetracarboxylate.

1. Melting point: above 300°C. (decomp.)
2. Elemental analysis values:

| | | | |
|---|---|---|---|
| Found:      | C 49.11%, | H 2.08%, | K 11.51% |
| Calculated: | C 49.13%, | H 2.06%, | K 11.42% |

4. Infrared absorption spectrum:
    Characteristic spectrum:
        3090, 2960 cm⁻¹ ($\nu$O—H)
        1695, 1400 cm⁻¹ ($\nu$C=O)
        1350, 1280, 1230, 1180, 1125, 930 cm⁻¹
        780, 760 cm⁻¹ ($\delta$C—H)

5. Difficultly soluble in water.

EXAMPLE 18

Ten parts of purified tetrapotassium 1,3,5,7-naphthalenetetracarboxylate obtained in the same way as in Example 7 was dissolved in 90 parts of water. The solution was maintained at 60°C. with stirring, and 5 parts of 6N hydrochloric acid was added gradually. After the addition, the stirring was continued further for 10 minutes. Then, the reaction mixture was cooled to room temperature. The resulting slurry was filtered, and the solid separated was washed with small amount of water and thoroughly dried at 110°C. to form 5.5 parts of white needle-like crystals. The product had the following properties.

1. The elemental analysis values of these crystals corresponded to those of dipotassium 1,3,5,7-naphthalenetetracarboxylate, as shown in the following.

| | C (%) | H (%) | K (%) |
|---|---|---|---|
| Found:      | 44.12 | 1.60 | 20.60 |
| Calculated: | 44.20 | 1.59 | 20.56 |

2. Infrared absorption spectrum: Shown in FIG. 6 of the accompanying drawings.
3. An X-ray diffraction analysis of these crystals showed that these crystals are not a mixture of 1,3,5,7-naphthalenetetracarboxylic acid or its monopotassium salt or tetrapotassium salt, but pure dipotassium 1,3,5,7-naphthalenetetracarboxylate.
4. When the crystals obtained were heat decomposed at 400°C. for 30 minutes in a stream of carbon dioxide, dipotassium 2,6-naphthalenedicarboxylate was obtained. Thus, it was confirmed that these crystals were 3,7-dipotassium 1,3,5,7-naphthalenetatracarboxylate.

EXAMPLES 19 and 20

4.7 parts (0.01 mol parts) of tetrapotassium 1,3,5,7-naphthalenetetracarboxylate was dissolved in 100 parts of water, and the solution was maintained at 30°C. With stirring, 1.7 parts (0.01 mol part) or 3.3 parts (0.02 mol part) respectively of 6N hydrochloric acid was added to the solution to perform acid precipitation. The solution was stirred for an additional 30 minutes at 30°C. The resulting slurry was filtered, and the solid separated was sufficiently dried at 110°C. to form crystals of 3,7-dipotassium 1,3,5,7-naphthalenetetracarboxylate, as shown in Table 8.

Table 8

| Example | 6 N hydrochloric acid | | | Product | | |
|---|---|---|---|---|---|---|
| | Parts by weight | Parts by mol | Mol ratio | Parts by weight | K content(%) | Name of substance |
| 19 | 1.7 | 0.01 | 1 | 2.0 | 20.7 | 3,7-dipotassium 1,3,5,7-naphthalene-tetracarboxylate |
| 20 | 3.3 | 0.02 | 2 | 3.7 | 20.6 | " |

EXAMPLE 21

20 Parts of purified tetramethyl 1,3,5,7-naphthalenetetracarboxylate obtained in the same way as in Example 14 was heated with stirring for 4 hours at the boiling point at atmospheric pressure together with 80 parts of water, 80 parts of methanol and 17.6 parts of sodium hydroxide. After the reaction, the water and methanol were evaporated off, and the reaction mixture was dried, followed by washing with a mixture of 10 parts of water and 90 parts of methanol. The washed mixture was dried for one day at 150°C. to form 20.8 parts of white needle-like crystals which had the following properties and were found to be substantially pure tetrasodium 1,3,5,7-naphthalenetetracarboxylate.
1. Melting point: above 300°C. (stable at around 400°C.)
2. Elemental analysis values: Found: C,42.81%; H,1.06%; Na,23.29%. Calculated: C,42.88%; H,1.03%; Na,23.45%.
3. Infrared absorption spectrum:
1615, 1580, 1550, 1385 cm$^{-1}$ ($\nu$C=O, $\nu$C—O)
790, 710 cm$^{-1}$ ($\delta$C—H)

EXAMPLE 22

Ten parts (0.029 mol part) of the tetrasodium 1,3,5,7-naphthalenetetracarboxylate obtained in Example 21 was dissolved in 100 parts of water, and with thorough stirring, 4.2 parts (0.025 mol part) of 6N hydrochloric acid was added gradually to this solution at room temperature. The solid precipitated was separated by filtration, and dried sufficiently at 150°C. to form 3.3 parts of white crystals. The elemental analysis values found for these crystals were: C 48.26%, H 2.36%, Na 13.24%. It was thus confirmed that these crystals were 3,7-disodium 1,3,5,7-naphthalenetetracarboxylate.

EXAMPLE 23

20 Parts of purified tetrapotassium 1,3,5,7-naphthalenetetracarboxylate obtained in the same way as in Example 7 was dissolved in 180 parts of water, and the solution was heated to 60°C. With thorough stirring, 4.8 parts of acetic acid was gradually added to the solution, and then the mixture was cooled to room temperature. The solid precipitated was separated by filtration, and thoroughly dried at 110°C. to form 14 parts of 3,7-dipotassium 1,3,5,7-naphthalenetetracarboxylate.

EXAMPLES 24 to 28

Ten parts of tetrapotassium 1,3,5,7-naphthalenetetracarboxylate was subjected to acid precipitation at room temperature using the medium and the organic acid shown in Table 9 below. The solid precipitated was separated by filtration, and dried to form 3,7-dipotassium 1,3,5,7-naphthalenetetracarboxylate in the amount indicated in Table 9.

mospheric pressure and refluxed for one hour. The solution was then cooled to room temperature. The precipitate was separated by filtration, and dried to form 25 parts of white needle-like crystals. The elemental analysis values found for these crystals were: C,44.22%; H,1.60%; K,20.51%; and substantially corresponded with those calculated for dipotassium 1,3,5,7-naphthalenetetracarboxylate which are C 44.20%, H 1.59%, K 20.56%.

An X-ray diffraction analysis of these crystals showed that these crystals hardly contain unreacted 1,3,5,7-naphthalenetetracarboxylic acid or its tetrapotassium salt, and are substantially pure dipotassium 1,3,5,7-naphthalenetetracarboxylate.

Het Heat of these crystals yielded dipotassium 2,6-naphthalenedicarboxylate, and this fact led to the confirmation that these crystals are 3,7-dipotassium 1,3,5,7-naphthalenetetracarboxylate.

EXAMPLE 30

To 100 parts of 50% water-containing methanol were added 3 parts of 1,3,5,7-naphthalenetetracarboxylic acid and 5 parts of tetrapotassium 1,3,5,7-naphthalenetetracarboxylate. The mixture was heated to 60°C., and stirred for 1 hour. Then, it was cooled to room temperature, and the precipitate was separated by filtration, washed with a small amount of methanol, and dried to form 7.5 parts of substantially pure 3,7-dipotassium 1,3,5,7-naphthalenetetracarboxylate.

EXAMPLE 31

3 Parts of tetrapotassium 1,3,5,7-naphthalenetetracarboxylate was suspended in 100 parts of methanol, and the suspension was heated to 60°C. With stirring, 1.1 parts of 6N hydrochloric acid was added to the suspension, and the mixture was heated at the boiling point for 1 hour. The mixture was cooled to room temperature (15°C.), and filtered. The cake obtained was washed with 50 parts of methanol, and dried to form 2.6 parts of white needle-like crystals which had the following properties and were found to be substantially pure tripotassium 1,3,5,7-naphthalenetetracarboxylate.
1. Melting point: More than 300°C. (decomp.)
2. Acid value 165 KOH mg/g (calculated, 163 KOH mg/g)

Table 9

| | Medium | | Organic acid | | Product | |
|---|---|---|---|---|---|---|
| Examples | Type | Amount (parts) | Type | Amount (parts) | Amount yielded (parts) | K content (%) |
| 24 | 50% water-containing methanol | 500 | Acetic acid | 5 | 7.1 | 20.5 |
| 25 | Water | 90 | Formic acid | 2 | 7.9 | 20.6 |
| 26 | 50% water-containing acetone | 500 | Chloroacetic acid | 4 | 7.2 | 20.6 |
| 27 | Water | 90 | o-Chlorobenzoic acid | 7 | 7.7 | 20.5 |
| 28 | Water | 90 | Benzenesulfonic acid | 7 | 7.6 | 20.4 |

EXAMPLE 29

Ten parts of 1,3,5,7-naphthalenetetracarboxylic acid was added to 150 parts of a 10% aqueous solution of tetrapotassium 1,3,5,7-naphthalenetetracarboxylate, and the mixture was heated to the boiling point at at- 3. Elemental analysis values:

| | C | H | K |
|---|---|---|---|
| Found: | 39.92% | 1.09% | 27.84% |
| Calculated: | 40.18% | 1.20% | 28.03% |

4. Infrared absorption spectrum:
1590, 1410, 1370, 1305, 1210 cm$^{-1}$ ($\nu$C=O, $\nu$C—O)

800, 775 cm$^{-1}$ ($\delta$C—H)

5. An X-ray diffraction analysis showed that these crystals exhibit quite a different diffraction pattern from that of tetrapotassium 1,3,5,7-naphthalenetetracarboxylate or dipotassium 1,3,5,7-naphthalenetetracarboxylate.
6. Easily decomposable in water.

EXAMPLE 32

5 Parts of tetrapotassium 1,3,5,7-naphthalenetetracarboxylate obtained in the same way as in Example 7 was dissolved in 95 parts of water, and the mixture warmed to 60°C. With stirring, an aqueous solution of 6 parts of Zn(NO$_3$)$_2$.6H$_2$O in 24 parts of water was gradually added to the mixture. On cooling, the precipitate was separated by filtration, washed with a small amount of water, and dried at 105°C. for one day. There were obtained 4.8 parts of white crystals, which were found by the following elemental analysis values to be dizinc 1,3,5,7-naphthalenetetracarboxylate dihydrate.

Elemental analysis values:
  C   35.94%   (calculated, 36.01%)
  H    1.69%   (calculated, 1.73%)
  Zn  28.12%   (calculated, 28.00%)

4 Parts of tetrapotassium 1,3,5,7-naphthalenetetracarboxylate, 3 parts of potassium carbonate and 2 parts of potassium chloride were mixed with 30 parts of potassium 1-naphthoate and 70 parts of potassium 2-naphthoate, and the mixture was heated at 440°C. for 5 hours in a carbon dioxide gas held at a pressure of 30 Kg/cm$^2$G to afford 72 parts of a rearrangement reaction product containing 16 parts of tetrapotassium 1,3,5,7-naphthalenetetracarboxylate dihydrate.

What we claim is:
1. A compound of the formula

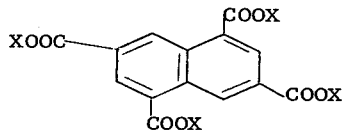

wherein the X's may be the same or different and are selected from the group consisting of hydrogen atoms, alkali metals, alkyl having 1 to 12 carbon atoms and allyl.

2. The compound of claim 1 which is 1,3,5,7-naphthalenetetracarboxylic acid.
3. The compound of claim 1 which is tetrapotassium 1,3,5,7-naphthalenetetracarboxylate.
4. The compound of claim 1 which is tetrasodium 1,3,5,7-naphthalenetetracarboxylate.
5. The compound of claim 1 which is tetramethyl 1,3,5,7-naphthalenetetracarboxylate.
6. The compound of claim 1 which is tetra-n-butyl 1,3,5,7-naphthalenetetracarboxylate.
7. The compound of claim 1 which is tetra-n-dodecyl 1,3,5,7-naphthalenetetracarboxylate.

8. The compound of claim 1 which is 3,7-dialkali metal 1,3,5,7-naphthalenetetracarboxylate of the formula

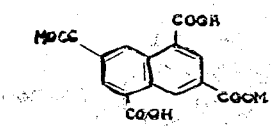

wherein M is an alkali metal.

9. The compound of claim 8 wherein said dialkali metal salt is 3,7-dipotassium 1,3,5,7-naphthalenetetracarboxylate.
10. The compound of claim 8 wherein said dialkali metal salt is 3,7-disodium 1,3,5,7-naphthalenetetracarboxylate.
11. A process for preparing an alkali metal 1,3,5,7-naphthalenetetracarboxylate of the formula

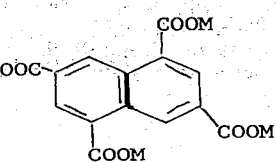

wherein M is an alkali metal, which comprises heating a mixture of at least one alkali metal naphthalenecarboxylate of the formula

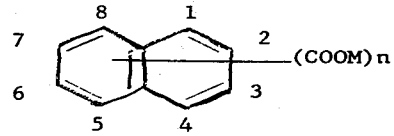

wherein n is an integer of 1 to 4; and M is an alkali metal with the proviso that when n is 4, the four —COOM groups are not present simultaneously at the 1,3,5,7-positions, and 1–40% by weight, based on the weight of the mixture, of said alkali metal 1,3,5,7-naphthalenetatracarboxylate to a temperature of at least 350°C. in an atmosphere of an inert gas and in the presence of a catalyst selected from the group consisting of the halides, oxides, sulfates, carbonates and carboxylates of zinc or cadmium and recovering the resulting alkali metal 1,3,5,7-naphthalenetetracarboxylate from the reaction mixture.

12. A process for preparing an alkali metal 1,3,5,7-naphthalenetetracarboxylate of high purity, which comprises heating at least one alkali metal naphthalenecarboxylate of the formula

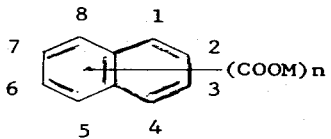

wherein $n$ is an integer of 1 to 4; and M is an alkali metal with the proviso that when $n$ is 4, the four —COOM groups are not present simultaneously in the 1,3,5,7-positions, to a temperature of at least 350°C. in an atmosphere of an inert gas, dissolving the reaction mixture obtained in water, adjusing the alkali ion concentration of the resulting aqueous solution to at least 6 g-alkali ion/ 1000 g-water, hot filtering the solid substance precipitated, then precipitating an alkali metal 1,3,5,7-naphthalenetetracarboxylate from the resulting filtrate, and recovering the alkali metal salt precipitated from the formed slurry.

13. A process for preparing a 3,7-dialkali 1,3,5,7-naphthalenetetracarboxylate of the formula

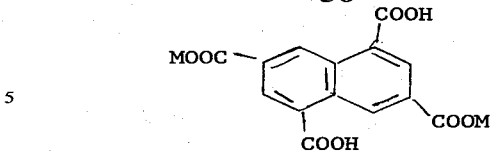

wherein M is an alkali metal, which comprises bringing a tetraalkali metal 1,3,5,7-naphthalenetetracarboxylate of the formula

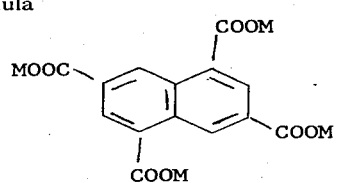

wherein M is the same as defined above, into contact with a mineral acid in an amount of not more than 2.5 equivalents per mol of the tetraalkali metal 1,3,5,7-carboxylate or an organic acid having a pKa value of not more than 5.4 in an aqueous medium.

14. A process for preparing a 3,7-dialkali metal 1,3,5,7-naphthalenetetracarboxylate, which comprises reacting 1,3,5,7-naphthalenetetracarboxylic acid or a monoalkali metal salt thereof or a mixture of said acid and said salt with a tetraalkali metal 1,3,5,7-naphthalenetetracarboxylate.

* * * * *

UNITED STATES PATENT AND TRADEMARK OFFICE
CERTIFICATE OF CORRECTION

PATENT NO. : 3,954,840
DATED : May 4, 1976
INVENTOR(S) : Gentaro Yamashita et al It is certified that error appears in the above-identified patent and that said Letters Patent are hereby corrected as shown below:

Claim 8, line 1, after "is" insert -- a --

Claim 8, delete the formula in its entirety, insert the following therefor:

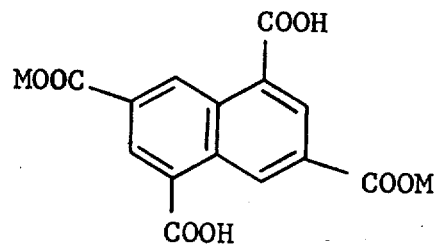

Claim 11, column 34, line 62, delete "thalenetatracarboxylate", insert -- thalenetetracarboxylate --

Signed and Sealed this

Thirty-first Day of August 1976

[SEAL]

Attest:

RUTH C. MASON
Attesting Officer

C. MARSHALL DANN
Commissioner of Patents and Trademarks